United States Patent
Mueller et al.

(10) Patent No.: US 10,588,976 B2
(45) Date of Patent: *Mar. 17, 2020

(54) ANTI-CD40 ANTIBODY FORMULATION

(71) Applicants: Claudia Mueller, Basel (CH); Matthias Willmann, Basel (CH)

(72) Inventors: Claudia Mueller, Basel (CH); Matthias Willmann, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/142,831

(22) Filed: Sep. 26, 2018

(65) Prior Publication Data

US 2019/0151450 A1    May 23, 2019

Related U.S. Application Data

(63) Continuation of application No. 15/881,195, filed on Jan. 26, 2018, now Pat. No. 10,111,958, which is a continuation of application No. 14/397,740, filed as application No. PCT/IB2013/053490 on May 2, 2013, now abandoned.

(60) Provisional application No. 61/642,644, filed on May 4, 2012.

(51) Int. Cl.
| A61K 39/395 | (2006.01) |
|---|---|
| C07K 16/28 | (2006.01) |
| A61K 47/26 | (2006.01) |
| A61K 47/18 | (2017.01) |
| A61K 9/19 | (2006.01) |
| A61K 47/22 | (2006.01) |
| A61K 39/00 | (2006.01) |

(52) U.S. Cl.
CPC ............ *A61K 47/26* (2013.01); *A61K 9/19* (2013.01); *A61K 39/3955* (2013.01); *A61K 39/39558* (2013.01); *A61K 39/39591* (2013.01); *A61K 47/183* (2013.01); *A61K 47/22* (2013.01); *C07K 16/2878* (2013.01); *A61K 2039/505* (2013.01); *C07K 2317/21* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| 6,923,956 B1 | 8/2005 | Tschope et al. |
|---|---|---|
| 8,277,810 B2 | 10/2012 | Long et al. |
| 8,333,970 B2 | 12/2012 | Aukerman et al. |
| 8,637,032 B2 | 1/2014 | Long et al. |
| 8,828,396 B2 | 9/2014 | Heusser et al. |
| 10,111,958 B2 | 10/2018 | Mueller et al. |
| 2004/0191243 A1 | 9/2004 | Chen et al. |
| 2005/0053598 A1 | 3/2005 | Burke et al. |
| 2006/0088523 A1 | 4/2006 | Andya et al. |
| 2008/0057070 A1 | 3/2008 | Long et al. |
| 2009/0202531 A1 | 8/2009 | Aukerman et al. |
| 2010/0203056 A1 | 8/2010 | Irving et al. |
| 2010/0254985 A1 | 10/2010 | Allan et al. |
| 2010/0322927 A1 | 12/2010 | Hansen et al. |
| 2013/0209480 A1 | 8/2013 | Mpofu et al. |
| 2014/0004131 A1 | 1/2014 | Mueller et al. |
| 2014/0186373 A1 | 7/2014 | Cosenza et al. |
| 2014/0205602 A1 | 7/2014 | Long et al. |
| 2014/0341898 A1 | 11/2014 | Heusser et al. |
| 2015/0086559 A1 | 3/2015 | Mueller et al. |

FOREIGN PATENT DOCUMENTS

| WO | 97/004801 A2 | 2/1997 |
|---|---|---|
| WO | 2003/040170 A2 | 5/2003 |
| WO | 2005/044306 A2 | 5/2005 |
| WO | 2005/044854 A2 | 5/2005 |
| WO | 2006/073443 A2 | 7/2006 |
| WO | 2006/125117 A2 | 11/2006 |
| WO | 2007/053661 A2 | 5/2007 |
| WO | 2007/124299 A2 | 11/2007 |
| WO | 2008/150494 A2 | 12/2008 |
| WO | 2009/062054 A1 | 5/2009 |
| WO | 2009/134776 | 5/2009 |
| WO | 2011/028811 A2 | 3/2011 |
| WO | 2011/050262 A2 | 4/2011 |
| WO | 2011/147921 A1 | 12/2011 |
| WO | 2012/003470 A2 | 1/2012 |
| WO | 2012/047954 A1 | 4/2012 |
| WO | 2012/065950 A2 | 5/2012 |

OTHER PUBLICATIONS

Li et al., "Promises and Obstacles for the Blockade of CD40-CD40L Interactions in Allotransplantation," Transplantation 86(1):10-15 (2008).
International Search Report and Written Opinion for International Application No. PCT/IB2013/053490 dated Dec. 4, 2013. 10 pages.

*Primary Examiner* — Phillip Gambel

(57) ABSTRACT

Anti-CD40 antibodies are formulated as lyophilisate or liquid formulation. The lyophilisates can be reconstituted to give a solution with a high concentration of the antibody active ingredient for delivery to a patient without high levels of antibody aggregation. The lyophilisate can be reconstituted with an aqueous reconstituent to provide an aqueous composition in which the antibody has a concentration of at least 50 mg/ml. The lyophilisate or aqueous pharmaceutical composition may include one or more of a sugar, a buffering agent, a surfactant, and/or a free amino acid.

7 Claims, No Drawings
Specification includes a Sequence Listing.

ANTI-CD40 ANTIBODY FORMULATION

CROSS-REFERENCE TO RELATED APPLICATIONS

This application is continuation of U.S. patent application Ser. No. 15/881,195, filed Jan. 26, 2018, now U.S. Pat. No. 10,111,958, which is a continuation of U.S. patent application Ser. No. 14/397,740, filed Oct. 29, 2014, which is a National Stage Entry of International Application No. PCT/IB2013/053490, filed May 2, 2013, which claims priority to U.S. Provisional Application No. 61/642,644, filed May 4, 2012, the contents of which are incorporated herein by reference in their entireties.

TECHNICAL FIELD

The present invention relates to a pharmaceutical formulation of an antibody against CD40, a process for the preparation thereof and uses of the formulation.

BACKGROUND

Despite the availability of several immunosuppressive treatments for autoimmune diseases, there remains a large unmet need for more efficacious and safer drugs in a large fraction of the patient population. For example, despite the reported efficacy of B cell depleting/inhibiting therapies like Rituximab and Belimumab in rheumatoid arthritis, systemic lupus erythematosus, Sjögren's syndrome, and multiple sclerosis, these therapies are only effective in a portion of diseased individuals, and with Rituximab, with an accompanying risk of progressive multifocal leukoencephalopathy. Further, multiple other leukocyte cell types are often involved in the pathology of these autoimmune diseases such as macrophages, dendritic cells and T cells, therefore therapeutic intervention targeting additional cell types or key immunological pathways that would inhibit their function could provide benefit. Given the multiple immunologically relevant roles of CD40-CD154 in the activation and function or these cell types, it is likely that an anti-CD40 antibody would confer therapeutic benefit to patients suffering autoimmune diseases outlined above beyond that currently provided by current therapies. Further, the central role for CD40-CD154 interactions in intestinal inflammatory disorders such as Crohn's disease and ulcerative colitis, and mechanistic links of the CD40 pathway to pathology in more rare disorders such as autoimmune vasculitis, pemphigus vulgaris, and idiopathic thrombocytopenic purpura (ITP) also highlights the potential of anti-CD40 antibodies in these indications.

The currently available immunosuppressants used after solid organ transplantation provide excellent short-term efficacy. Acute rejections within the de novo period are observed in 5%-20% of the recipients (depending on organ, patient population, and regimen) and the proportion of grafts lost to acute rejection within the de novo period is below 5% for any setting. Currently the key unmet need is the tolerability of immunosuppression with patient and graft survival in the long term. After renal transplant, 33% patients die and/or lose their graft within 5 years; the average age of death of transplant recipient is 58 years. Calcineurin inhibitors (CNI) remain the mainstay of immunosuppressive therapy for the vast majority of transplant patients. While nephrotoxicity and cardiovascular morbidity associated with CNIs is one of the drivers of chronic allograft nephropathy as well as patient death with a functioning graft, alternative primary immunosuppression have not been able to replace CNIs. Overall, there is still room for improvement in long-term transplant immunosuppression. B-cell mediated immunological damage of transplanted kidneys may contribute to poor long-term outcomes and the need for new agents to target B-cell rejection is increasingly recognised by the medical community.

Antibodies against CD40 are known in the art. Chir12.12 is a fully humanised, non-agonist anti-CD40 antibody (IgG1, kappa) that blocks CD154 (also known as CD40 ligand; CD40L)-mediated leukocyte activation and can mediate antibody-dependent cellular cytotoxicity (ADCC) of human leukocytes and B cell lymphomas in vitro (see WO 2006/073443). WO 2005/044306 describes anti-CD40 antagonist antibodies, including Chir12.12 for use in particular in the treatment of autoimmune and inflammatory disorders. Further Chir12.12 is effective in delaying kidney allograft rejection when dosed as a monotherapy in *Macaca fascicularis* (Cynomolgus monkeys) [Li et al. (2008) Transplantation; 86 (1):10-15]. However, Chir12.12 can also mediate depletion of peripheral B cells in non human primates (NHPs).

Anti-CD40 mAbs with silenced ADCC activity are predicted to have an improved safety profile relative to the parental anti-CD40 antibodies, and in particular may be more suitable for non-oncologic indications, such as autoimmune diseases and use in a transplant setting. The applicant has developed three silent anti-CD40 antibodies based on the Chir12.12 antibody. These antibodies, hereinafter designated mAb1, mAb2 and mAb3 are characterised by certain amino acid mutations in the Fc region which silence ADCC activity.

mAb1 comprises an N297A mutation in the antibody heavy chain amino acid sequence. The antibody comprises the heavy chain CDR1, CDR2 and CDR3 of SEQ ID NOs 3, 4 and 5 respectively, and light chain CDR1, CDR2 and CDR3 of SEQ ID NOs: 6, 7 and 8, respectively. mAb1 comprises a $V_H$ domain with the amino acid sequence of SEQ ID NO: 1 and a $V_L$ domain with the amino acid sequence of SEQ ID NO: 2. mAb1 comprises the full length heavy chain amino acid sequence of SEQ ID NO: 9 and the full length light chain amino acid sequence of SEQ ID NO: 10.

mAb2 comprises a D265A mutation in the antibody heavy chain amino acid sequence. The antibody comprises the heavy chain CDR1, CDR2 and CDR3 of SEQ ID NOs 3, 4 and 5 respectively, and light chain CDR1, CDR2 and CDR3 of SEQ ID NOs: 6, 7 and 8, respectively. mAb2 comprises a $V_H$ domain with the amino acid sequence of SEQ ID NO: 1 and a $V_L$ domain with the amino acid sequence of SEQ ID NO: 2. mAb2 comprises the full length heavy chain amino acid sequence of SEQ ID NO: 13 and the full length light chain amino acid sequence of SEQ ID NO: 14.

mAb3 comprises a L234A, L235A mutation (LALA) in the antibody heavy chain amino acid sequence. The antibody comprises the heavy chain CDR1, CDR2 and CDR3 of SEQ ID NOs 3, 4 and 5 respectively, and light chain CDR1, CDR2 and CDR3 of SEQ ID NOs: 6, 7 and 8, respectively. mAb3 comprises a $V_H$ domain with the amino acid sequence of SEQ ID NO: 1 and a $V_L$ domain with the amino acid sequence of SEQ ID NO: 2. mAb3 comprises the full length heavy chain amino acid sequence of SEQ ID NO: 17 and the full length light chain amino acid sequence of SEQ ID NO: 18.

Formulations with high concentration of antibody may have short shelf lives and the formulated antibodies may lose biological activity resulting from chemical and physical instabilities during the storage. Among those, aggregation, deamidation and oxidation are known to be the most common causes of antibody degradation. In particular, aggregation can potentially lead to increased immune response in patients, leading to safety concerns. Thus it must be minimised or prevented.

It is an object of the invention to provide further and improved formulations of anti-CD40 antibodies, and in particular formulations with high concentration of anti-CD40 antibodies and low levels of antibody aggregation.

DISCLOSURE OF THE INVENTION

Therapeutic antibodies are typically formulated either in aqueous form ready for parenteral administration or as lyophilisates for reconstitution with a suitable diluent prior to administration. According to the invention, an anti-CD40 antibody may be formulated either as a lyophilisate, or as an aqueous composition, for example in pre-filled syringes. Suitable formulation can provide an aqueous pharmaceutical composition or a lyophilisate which can be reconstituted to give a solution with a high concentration of the antibody active ingredient and a low level of antibody aggregation for delivery to a patient. High concentrations of antibody are useful as they reduce the amount of material which must be delivered to a patient. Reduced dosing volumes minimise the time taken to deliver a fixed dose to the patient. The aqueous compositions of the invention with high concentration of anti-CD40 antibodies are particularly suitable for subcutaneous administration.

Thus the invention provides an aqueous pharmaceutical composition, suitable for parenteral administration in a subject, e.g., for subcutaneous administration, comprising an anti-CD40 antibody.

The following specific embodiments of the invention are described as numbered hereafter:

1. An aqueous pharmaceutical composition, suitable for subcutaneous administration in a subject, comprising an anti-CD40 antibody in which the antibody has a concentration of at least 50 mg/ml, and wherein said anti-CD40 antibody includes: (i) one or more heavy chain CDRs selected from the group consisting of SEQ ID NOs: 3, 4 and 5; and/or (ii) one or more light chain CDRs selected from the group consisting of SEQ ID NOs: 6, 7 and 8.
2. The aqueous pharmaceutical composition, suitable for subcutaneous administration in a subject, according to Embodiment 1, wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8.
3. The aqueous pharmaceutical composition of Embodiment 1 or 2, wherein the anti-CD40 antibody comprises a $V_H$ domain with amino acid SEQ ID NO: 1 and a $V_L$ domain with amino acid SEQ ID NO: 2.
4. The aqueous pharmaceutical composition of Embodiment 1, 2 or 3, wherein the anti-CD40 antibody comprises a heavy chain region of SEQ ID NO: 9 and a light chain region of SEQ ID NO: 10, or a heavy chain region of SEQ ID NO: 13 and a light chain region of SEQ ID NO: 14, or a heavy chain region of SEQ ID NO: 17 and a light chain region of SEQ ID NO: 18.
5. The aqueous pharmaceutical composition of any one of Embodiments 1 to 4, wherein less than 5% of the anti-CD40 antibody is aggregated or degraded.
6. The aqueous pharmaceutical composition of any one of Embodiments 1 to 5, comprising one or more of the following components selected among the group consisting of: a stabiliser, a buffering agent; and a surfactant.
7. The aqueous pharmaceutical composition of Embodiment 6, wherein the stabiliser is a sugar.
8. The aqueous pharmaceutical composition of Embodiment 6 or 7, comprising: a sugar, a buffering agent, and a surfactant.
9. The aqueous pharmaceutical composition of Embodiment 6 or 7, further comprising a free amino acid.
10. The aqueous pharmaceutical composition of Embodiment 7 to 9, comprising sucrose as a sugar.
11. The aqueous pharmaceutical composition of Embodiment 10, comprising 200-300 mM sucrose.
12. The aqueous pharmaceutical composition of Embodiments 6-11, comprising a histidine buffer as the buffering agent.
13. The aqueous pharmaceutical composition of Embodiment 12, comprising 25-35 mM histidine buffer.
14. The aqueous pharmaceutical composition of Embodiments 6 to 13, comprising polysorbate 20 as a surfactant.
15. The aqueous pharmaceutical composition of Embodiment 14, comprising 0.01 to 0.2% polysorbate 20.
16. The aqueous pharmaceutical composition of Embodiment 9, further comprising arginine and/or methionine as free amino acid.
17. The aqueous pharmaceutical composition of Embodiment 16, comprising 40-80 mM arginine.
18. The aqueous pharmaceutical composition of any preceding Embodiment, comprising sucrose, a histidine buffer, polysorbate 20 and arginine.
19. The aqueous pharmaceutical composition of any preceding Embodiment, comprising sucrose, a histidine buffer, polysorbate 20 and methionine.
20. The aqueous pharmaceutical composition of any preceding Embodiment, comprising sucrose, a histidine buffer, polysorbate 20, arginine and methionine.
21. A lyophilisate suitable for preparing the aqueous pharmaceutical composition of any preceding Embodiments.
22. A lyophilisate according to Embodiment 21, comprising sucrose, a histidine buffer, and polysorbate 20.
23. A method for preparing a lyophilisate, comprising the steps of: (i) preparing an aqueous solution comprising an anti-CD40 antibody, a sugar, a buffering agent, a surfactant and optionally a free amino acid; and (ii) lyophilising the aqueous solution.
24. A delivery device including the aqueous pharmaceutical composition of any one of Embodiments 1-20.
25. A pre-filled syringe including the aqueous pharmaceutical composition of any one of Embodiments 1-20.
26. A method for delivering an anti-CD40 monoclonal antibody to a mammal, comprising a step of administering to the patient a pharmaceutical composition of any one of Embodiments 1-20.
27. The composition of any one of Embodiments 1-20, for use in treating a disease or disorder that is mediated by CD40.
28. The composition of Embodiment 27, for the treatment of autoimmune diseases.
29. The composition of Embodiment 28, for the treatment of rheumatoid arthritis, systemic lupus erythematosus, or Pemphigus vulgaris.
30. The aqueous pharmaceutical composition of any one of Embodiments 1-20 in which the antibody has a concentration of at least at least 50 mg/ml, at least 100 mg/ml, at least 150 mg/ml, at least 200 mg/ml, at least 250 mg/ml, or at least 300 mg/ml.

The invention also provides an aqueous pharmaceutical composition comprising: an anti-CD40 monoclonal antibody as described above, for example mAb1, mAb2 or mAb3, especially mAb1; a stabiliser; a buffering agent; and a surfactant. The composition preferably also includes a free amino acid.

The invention also provides a lyophilisate comprising: an anti-CD40 monoclonal antibody as described above, for example mAb1, mAb2 or mAb3, especially mAb1; a sugar; a buffering agent; and a surfactant. The lyophilisate preferably also includes a free amino acid.

The invention also provides a lyophilisate comprising an anti-CD40 monoclonal antibody as described above, for example mAb1, mAb2 or mAb3, especially mAb1; wherein the lyophilisate can be reconstituted with an aqueous reconstituent to provide an aqueous composition in which the antibody has a concentration of at least 50 mg/ml, 100 mg/ml, 150 mg/ml, 200 mg/ml, 250 mg/ml, or 300 mg/ml, after reconstitution in an aqueous solution.

The invention also provides an aqueous pharmaceutical composition comprising high concentration of an anti-CD40 monoclonal antibody as described above, for example mAb1, mAb2 or mAb3, especially mAb1; wherein less than 5%, 4%, 3%, 2% or 1% of the anti-CD40 antibody is aggregated or degraded.

The invention also provides a process for preparing a lyophilisate, comprising steps of: (i) preparing an aqueous solution comprising an anti-CD40 monoclonal antibody, a sugar, a buffering agent, a surfactant, and optionally a free amino acid; and (ii) lyophilising the aqueous solution.

The invention also provides a process for preparing a pharmaceutical composition, comprising a step of mixing a lyophilisate with an aqueous reconstituent, wherein the lyophilisate comprises an anti-CD40 monoclonal antibody, a sugar, a buffering agent, a surfactant, and optionally a free amino acid.

More specifically the invention provides a lyophilised formulation prepared by lyophilising an aqueous formulation having a pH of 5.0-7.0 and comprising
(i) an anti-CD40 antibody wherein the antibody has a concentration of 20-150 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) a stabiliser,
(iii) a buffering agent,
(iv) a surfactant, and optionally
(v) an amino acid.

In one embodiment said formulation is prepared from an aqueous formulation having a pH of 5.0-7.0 and comprising
(i) an anti-CD40 antibody wherein the antibody has a concentration of 20-150 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) sucrose or trehalose as a stabiliser,
(iii) histidine as a buffering agent,
(iv) polysorbate 20 as a surfactant, and optionally
(v) an amino acid selected from arginine, methionine and glycine.

In one embodiment said lyophilised formulation is prepared from an aqueous formulation having a pH of 5.0-7.0 and comprising
(i) an anti-CD40 antibody wherein the antibody has a concentration of 20-150 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 3-300 mM sucrose or trehalose as a stabiliser,
(iii) 1-60 mM histidine as a buffering agent,
(iv) up to 0.2% polysorbate 20 as a surfactant, and optionally
(v) 2-80 mM arginine, methionine or glycine.

In one embodiment said lyophilised formulation is prepared from an aqueous formulation having a pH of 6.0 and comprising
(i) an anti-CD40 antibody wherein the antibody has a concentration of 50 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 90 mM sucrose as a stabiliser,
(iii) 10 mM histidine as a buffering agent,
(iv) 0.02% polysorbate 20 as a surfactant.

In one embodiment said lyophilised formulation is prepared from an aqueous formulation having a pH of 6.0 and comprising
(i) an anti-CD40 antibody wherein the antibody has a concentration of 50 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 90 mM sucrose as a stabiliser,
(iii) 10 mM histidine as a buffering agent,
(iv) 0.02% polysorbate 20 as a surfactant, and
(v) 17 mM arginine.

In one embodiment said lyophilised formulation is prepared from an aqueous formulation having a pH of 6.0 and comprising
(i) an anti-CD40 antibody wherein the antibody has a concentration of 150 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 270 mM sucrose as a stabiliser,
(iii) 30 mM histidine as a buffering agent, and
(iv) 0.06% polysorbate 20 as a surfactant.

The invention also provides an aqueous pharmaceutical composition obtained by reconstituting a lyophilised formulation as described above, wherein the reconstitution factor is between 1:0.5 to 1:6.

In one embodiment the reconstitution factor is 1:3.

The invention also provides an aqueous pharmaceutical composition having a pH of 5.0 to 7.0 comprising
(i) an anti-CD40 antibody wherein the antibody has a concentration of at least 50 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) a stabiliser,
(iii) a buffering agent,
(iv) a surfactant, and optionally
(v) an amino acid.

In one embodiment the aqueous pharmaceutical composition having a pH of 5.0 to 7.0 comprises
(i) an anti-CD40 antibody wherein the antibody has a concentration of at least 50 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) sucrose or trehalose as a stabiliser,
(iii) histidine as a buffering agent,
(iv) polysorbate 20 as a surfactant, and optionally
(v) an amino acid selected from arginine, methionine or glycine.

In one embodiment the aqueous pharmaceutical composition having a pH of 5.0 to 7.0 comprises
(i) an anti-CD40 antibody wherein the antibody has a concentration of at least 50 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 200-300 mM sucrose as a stabiliser,
(iii) 25-35 mM histidine as a buffering agent,
(iv) up to 0.2% polysorbate 20 as a surfactant, and optionally
(v) 10-80 mM arginine, methionine or glycine.

In one embodiment the aqueous pharmaceutical composition has a pH of 6.0 and comprises
(i) an anti-CD40 antibody wherein the antibody has a concentration of at least 50 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 270 mM sucrose as a stabiliser,
(iii) 30 mM histidine as a buffering agent, and
(iv) 0.06% polysorbate 20 as a surfactant.

In one embodiment the aqueous pharmaceutical composition has a pH of 6.0 and comprises
(i) an anti-CD40 antibody wherein the antibody has a concentration of at least 50 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 270 mM sucrose as a stabiliser,
(iii) 30 mM histidine as a buffering agent,
(iv) 0.06% polysorbate 20 as a surfactant, and
(v) 51 mM arginine.

In one embodiment the aqueous pharmaceutical composition of the invention has an anti-CD40 antibody concentration of 150 mg/ml.

In one embodiment the lyophilised formulation or the aqueous pharmaceutical composition of the invention comprises a VH domain having the amino acid sequence of SEQ ID NO: 1 and a VL domain having the amino acid sequence of SEQ ID NO: 2.

In one embodiment the lyophilised formulation or the aqueous pharmaceutical composition of the invention comprises an anti-CD40 antibody comprising a heavy chain region of SEQ ID NO: 9 and a light chain region of SEQ ID NO: 10.

In one embodiment the lyophilised formulation or the aqueous pharmaceutical composition of the invention comprises the anti-CD40 antibody Chir12.12 having an N297A mutation.

In one embodiment the lyophilised formulation or the aqueous pharmaceutical composition of the invention comprises an anti-CD40 antibody comprising a heavy chain region of SEQ ID NO: 13 and a light chain region of SEQ ID NO: 14.

In one embodiment the lyophilised formulation or the aqueous pharmaceutical composition of the invention comprises the anti-CD40 antibody Chir12.12 having a D265A mutation.

In one embodiment the lyophilised formulation or the aqueous pharmaceutical composition of the invention comprises an anti-CD40 antibody comprising a heavy chain region of SEQ ID NO: 17 and a light chain region of SEQ ID NO: 18.

In one embodiment the lyophilised formulation or the aqueous pharmaceutical composition of the invention comprises the anti-CD40 antibody Chir12.12 having an L234A L235A mutation.

The invention also comprises a delivery device including the aqueous pharmaceutical composition of the invention.

The invention also comprises a pre-filled syringe including the aqueous pharmaceutical composition of the invention.

The invention also comprises a method for delivering an anti-CD40 antibody to a mammal, comprising a step of administering to the patient an aqueous pharmaceutical composition of the invention.

The invention also comprises a lyophilised formulation or an aqueous pharmaceutical composition according to the invention for use in treating a disease or disorder that is mediated by CD40.

The invention also comprises a lyophilised formulation or aqueous pharmaceutical composition according to the invention for use in the treatment of autoimmune diseases.

The invention also provides a lyophilised formulation or aqueous pharmaceutical composition according to the invention Multiple Sclerosis, Systemic Lupus Erythematosus, Sjögren's syndrome, Rheumatoid Arthritis, transplant rejection; graft-versus-host disease, Pemphigus vulgaris.

Aqueous Pharmaceutical Compositions with High Concentration of Anti-CD40 Antibodies The invention relies, at least partly, in the formulation properties of antibodies such as mAb1, which retain remarkable stability and bioactive properties when formulated in a high concentration either as a liquid (aqueous) or lyophilisate composition.

As used herein, an "aqueous" pharmaceutical composition is a composition suitable for pharmaceutical use, wherein the aqueous carrier is distilled water. A composition suitable for pharmaceutical use may be sterile, homogeneous and/or isotonic. Aqueous pharmaceutical compositions may be prepared either directly in an aqueous form, for example in pre-filled syringe ready for use (the "liquid formulations") or as lyophilisate to be reconstituted shortly before use. As used herein, the term "aqueous pharmaceutical composition" refers to the liquid formulation or reconstituted lyophilised formulation. In certain embodiments, the aqueous pharmaceutical compositions of the invention are suitable for parenteral administration to a human subject. In a specific embodiment, the aqueous pharmaceutical compositions of the invention are suitable for subcutaneous administration.

As used herein, the phrase "parenteral administration" means mode of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The use of antibodies as the active ingredient of pharmaceuticals is now widespread, including the products HERCEPTIN™ (trastuzumab), RITUXAN™ (rituximab), SYNAGIS™ (palivizumab), etc. Techniques for purification of therapeutic antibodies to a pharmaceutical grade are well known in the art.

The composition will usually be non-pyrogenic e.g. containing <1 EU (endotoxin unit, a standard measure) per dose, and preferably <0.1 EU per dose. The composition is preferably gluten-free.

In specific embodiments, the aqueous pharmaceutical compositions of the invention exhibit low to undetectable levels of antibody aggregation or degradation, with very little to no loss of the biological activities during manufacture, preparation, transportation and long periods of storage, the concentration of the anti-CD40 antibody being at least about 50 mg/ml, 100 mg/ml, 150 mg/ml, 200 mg/ml, 250 mg/ml, or 300 mg/ml.

In one aspect, the invention relates to an aqueous pharmaceutical composition with high concentration of anti-CD40 antibodies.

It is known in the art that such high concentration aqueous pharmaceutical compositions can be diluted prior to injection, for example, if lower antibody concentrations are required for specific therapeutic interventions or when treating patients of lower body weight including children. Suitable concentrations can be 25 mg/ml or 10 mg/ml. Alternatively, the original formulation may be produced with such a lower concentration.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three or four domains, depending on the isotype, $C_H1$, $C_H2$, $C_H3$ and $C_H4$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of CD40). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and $C_H1$ domains; a F(ab)$_2$ fragment, a bivalent fragment comprising two Fab fragments linked by a disulfide bridge at the hinge region; a Fd fragment consisting of the $V_H$ and $C_H1$ domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities, e.g., an isolated antibody that specifically binds human CD40 is substantially free of antibodies that specifically bind antigens other than CD40. An isolated antibody that specifically binds CD40 may, however, have cross-reactivity to other antigens, such as CD40 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86).

The structures and locations of immunoglobulin variable domains, e.g., CDRs, may be defined using well known numbering schemes, e.g., the Kabat numbering scheme, the Chothia numbering scheme, a combination of Kabat and Chothia (AbM), etc. (see, e.g., Sequences of Proteins of Immunological Interest, U.S. Department of Health and Human Services (1991), eds. Kabat et al.; A I Lazikani et al. (1997) J. Mol. Bio. 273:927 948). Throughout this specification, the complementarity determining region ("CDR") is defined according to the Kabat definition with the exception of CDRH1 which is the stretch of amino acids defined by a combination of both Kabat and Chothia definitions for this CDR.

The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgA, IgD, IgE and IgG such as IgG1, IgG2, IgG3 or IgG4) that is provided by the heavy chain constant region genes.

The phrases "an antibody recognising an antigen" and "an antibody specific for an antigen" are used interchangeably herein with the term "an antibody which binds specifically to an antigen".

As used herein, an antibody that "specifically binds to CD40 polypeptide" or an "anti-CD40 antibody" refers to an antibody that binds to human CD40 polypeptide of SEQ ID NO: 21 with a $K_D$ of 100 nM or less, 10 nM or less, 1 nM or less. An antibody that "cross-reacts with an antigen other than CD40" refers to an antibody that binds that antigen with a $K_D$ of $0.5 \times 10^{-8}$ M or less, $5 \times 10^{-9}$ M or less, or $2 \times 10^{-9}$ M or less. An antibody that "does not cross-react with a particular antigen" is intended to refer to an antibody that binds to that antigen, with a $K_D$ of $1.5 \times 10^{-8}$ M or greater, or a $K_D$ of $5$-$10 \times 10^{-8}$ M or $1 \times 10^{-7}$ M or greater. In certain embodiments, such antibodies that do not cross-react with the antigen exhibit essentially undetectable binding against these proteins in standard binding assays.

In one embodiment, a high concentration of an anti-CD40 antibody in the aqueous pharmaceutical composition of the invention is at least 50 mg/ml. In one embodiment, a high concentration is at least 100 mg/ml. In one embodiment, a high concentration is at least 150 mg/ml. In one embodiment, a high concentration is at least 200 mg/ml. In one embodiment, a high concentration is at least 250 mg/ml. In one embodiment, a high concentration is at least 300 mg/ml.

In one embodiment, the aqueous pharmaceutical composition of the invention comprises between 50 mg/ml and 300 mg/ml of an anti-CD40 antibody, for example, mAb1.

In one embodiment, the aqueous pharmaceutical composition of the invention comprises between 75 mg/ml and 250 mg/ml of an anti-CD40 antibody, for example, mAb1.

In one embodiment, the aqueous pharmaceutical composition of the invention comprises between 100 mg/ml and 250 mg/ml of an anti-CD40 antibody, for example, mAb1.

In one embodiment, the aqueous pharmaceutical composition of the invention comprises between 100 mg/ml and 200 mg/ml of an anti-CD40 antibody, for example, mAb1.

In one embodiment, the aqueous pharmaceutical composition of the invention comprises 150 mg/ml of an anti-CD40 antibody, for example, mAb1.

In one embodiment, the aqueous pharmaceutical composition of the invention comprises about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, about 160 mg/ml, about 170 mg/ml, about 180 mg/ml, about 190 mg/ml, about 200 mg/ml, about 210 mg/ml, about 220 mg/ml, about 230 mg/ml, about 240 mg/ml, about 250 mg/ml or about 300 mg/ml of an anti-CD40 antibody, for example, mAb1.

Furthermore, the aqueous pharmaceutical compositions are stable such that, even after storage for 4 weeks at 2-8° C., less than 5%, 4%, 3%, 2%, 1%, 0.05% or 0.01% of the total anti-CD40 antibody is aggregated as measured by SEC-HPLC.

The aqueous pharmaceutical compositions may include, in addition to the anti-CD40 antibody, further components such as one or more of the following: (i) a stabiliser; (ii) a buffering agent; (iii) a surfactant; and (iv) a free amino acid. Inclusion of each of such additional components can give compositions with low aggregation of the anti-CD40 antibody.

Suitable stabilisers for use with the invention can act, e.g., as viscosity enhancing agents, bulking agents, solubilising agents, and/or the like. The stabiliser can be ionic or non-ionic (e.g. sugars). As sugars they include, but are not limited to, monosaccharides, e.g., fructose, maltose, galactose, glucose, D-mannose, sorbose and the like; disaccharides, e.g. lactose, sucrose, trehalose, cellobiose, and the like; polysaccharides, e.g. raffinose, melezitose, maltodextrins, dextrans, starches, and the like; and alditols, such as mannitol, xylitol, maltitol, lactitol, xylitol sorbitol (glucitol) and the like. For example, the sugar may be sucrose, trehalose, raffinose, maltose, sorbitol or mannitol. The sugar may be a sugar alcohol or an amino sugar. Sucrose is particularly useful. As ionic stabiliser they include salts such as NaCl or amino acid components such as arginine-HCl.

Suitable buffering agents for use with the invention include, but are not limited to, organic acid salts such as salts of citric acid, ascorbic acid, gluconic acid, carbonic acid, tartaric acid, succinic acid, acetic acid or phtalic acid; Tris, thomethamine hydrochloride, or phosphate buffer. In addition, amino acid components can also be used as buffering agent. Such amino acid component includes without limitation glycine and histidine. A histidine buffer is particularly useful.

The aqueous pharmaceutical compositions include such buffering agent or pH adjusting agent to provide improved pH control. In one embodiment, an aqueous pharmaceutical composition of the invention has a pH between 5.0 and 8.0, between 5.5 and 7.5, between 5.0 and 7.0, between 6.0 and 8.0, or between 6.0 and 7.0. In a specific embodiment, an aqueous pharmaceutical composition of the invention has a pH of about 6.0.

As used herein, the term "surfactant" herein refers to organic substances having amphipathic structures; i.e., they are composed of groups of opposing solubility tendencies, typically an oil-soluble hydrocarbon chain and a water-soluble ionic group. Surfactants can be classified, depending on the charge of the surface-active moiety, into anionic, cationic and dispersing agents for various pharmaceutical compositions and preparations of biological materials.

Suitable surfactants for use with the invention include, but are not limited to, non-ionic surfactants, ionic surfactants and zwitterionic surfactants. Typical surfactants for use with the invention include, but are not limited to, sorbitan fatty acid esters (e.g. sorbitan monocaprylate, sorbitan monolaurate, sorbitan monopalmitate), sorbitan trioleate, glycerine fatty acid esters (e.g. glycerine monocaprylate, glycerine monomyristate, glycerine monostearate), polyglycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxyethylene polyoxypropylene alkyl ethers (e.g. polyoxyethylene polyoxypropylene glycol, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearic acid amide); $C_{10}$-$C_{18}$ alkyl sulfates (e.g. sodium cetyl sulfate, sodium lauryl sulfate, sodium oleyl sulfate), polyoxyethylene $C_{10}$-$C_{18}$ alkyl ether sulfate with an average of 2 to 4 moles of ethylene oxide units added (e.g. sodium polyoxyethylene lauryl sulfate), and $C_1$-$C_{18}$ alkyl sulfosuccinate ester salts (e.g. sodium lauryl sulfosuccinate ester); and natural surfactants such as lecithin, glycerophospholipid, sphingophospholipids (e.g. sphingomyelin), and sucrose esters of $C_{12}$-$C_{18}$ fatty acids. A composition may include one or more of these surfactants. Preferred surfactants are polyoxyethylene sorbitan fatty acid esters e.g. polysorbate 20, 40, 60 or 80. Polysorbate 80 (Tween 80) is particularly useful.

Suitable free amino acids for use with the invention include, but are not limited to, arginine, lysine, histidine, methionine, ornithine, isoleucine, leucine, alanine, glycine, glutamic acid or aspartic acid. The inclusion of a basic amino acid is preferred i.e. arginine, lysine and/or histidine. If a composition includes histidine then this may act both as a buffering agent and a free amino acid, but when a histidine buffer is used it is typical to include a non-histidine free amino acid e.g. to include histidine buffer and lysine. An amino acid may be present in its D- and/or L-form, but the L-form is typical. The amino acid may be present as any suitable salt e.g. a hydrochloride salt, such as arginine-HCl.

When present, components (i) to (iv) will be at a concentration sufficient to maintain the anti-CD40 antibody in a form which is active and soluble after either
(i) lyophilisation and storage and reconstitution (for lyophilisates), or
(ii) conditioning in dosing units and storage (for liquid formulations).

Thus a sugar may be present in the aqueous pharmaceutical composition of the invention, e.g. after reconstitution of a lyophilisate in water, at a concentration of between 3 and 400 mM e.g. 50-380 mM, 100-350 mM, 200-300 mM. A concentration of 270 mM sucrose is useful.

A buffering agent may be present in the aqueous pharmaceutical composition of the invention, e.g. after reconstitution of a lyophilisate in water, at a concentration of between 1 and 60 mM e.g. 10-50 mM, 20-40 mM, 25-35 mM. A concentration of 30 mM histidine buffer is useful.

A surfactant may be present in the aqueous pharmaceutical composition of the invention, e.g. after reconstitution of a lyophilisate in water, at a concentration of up to 0.2% (by volume) e.g. 0.01-0.1%, 0.03-0.08%, 0.04-0.08%. A concentration of 0.06% polysorbate 20 is useful. In some embodiments polysorbate 80 may be used.

A free amino acid may be present in the aqueous pharmaceutical composition of the invention, e.g. after reconstitution of a lyophilisate in water, at a concentration of between 2 and 100 mM e.g. 10-80 mM, 20-70 mM, 30-60 mM, 40-60 mM. A concentration of 51 mM arginine (e.g. arginine-HCl) or 60 mM methionine or glycine (e.g. glycine-HCl) is useful.

A formulation containing histidine buffer, sucrose and polysorbate 20 has been shown to be suitable for lyophilisation of antibody mAb1 at a concentration of at least 150 mg/ml after reconstitution.

In one embodiment the aqueous pharmaceutical composition consists of 150 mg/ml mAb1, 30 mM histidine, 270 mM sucrose and 0.06% polysorbate 20.

In one embodiment the aqueous pharmaceutical composition consists of 150 mg/ml mAb1, 30 mM histidine, 270 mM sucrose, 0.06% polysorbate 20 and 51 mM arginine-HCl.

In one embodiment the aqueous pharmaceutical composition consists of 150 mg/ml mAb1, 30 mM histidine, 270 mM sucrose, 0.06% polysorbate 20 and 60 mM glycine-HCl.

In one embodiment the aqueous pharmaceutical composition consists of 200 mg/ml mAb1, 30 mM histidine, 270 mM sucrose, and 0.06% polysorbate 20.

In one embodiment the aqueous pharmaceutical composition consists of 200 mg/ml mAb1, 30 mM histidine, 270 mM sucrose, 0.06% polysorbate 20 and 51 mM arginine-HCl.

In one embodiment the aqueous pharmaceutical composition consists of 75 mg/ml mAb1, 30 mM histidine, 270 mM sucrose, and 0.06% polysorbate 20.

In one embodiment the aqueous pharmaceutical composition consists of 75 mg/ml mAb1, 30 mM histidine, 270 mM sucrose, 0.06% polysorbate 20 and 51 mM arginine-HCl.

Other contemplated excipients, which may be utilised in the aqueous pharmaceutical compositions of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, $4^{th}$ edition, Rowe et al., Eds., American Pharmaceuticals Association (2003); and Remington: the Science and Practice of Pharmacy, $21^{th}$ edition, Gennaro, Ed., Lippincott Williams & Wilkins (2005).

The aqueous pharmaceutical compositions of the invention may include further active ingredients in addition to the anti-CD40 antibody. Further pharmacological agents may include, for instance, chemotherapeutic compounds.

Lyophilisates

Techniques for lyophilisation of antibodies are well known in the art e.g. see John F. Carpenter and Michael J. Pikal, 1997 (*Pharm. Res.* 14, 969-975); Xialin (Charlie) Tang and Michael J. Pikal, 2004 (*Pharm. Res.* 21, 191-200). For example, the monoclonal antibody products SYNAGIS™, REMICADE™, RAPTIVA™, SIMULECT™, XOLAIR™ and HERCEPTIN™ are supplied as lyophilisates. These antibodies are reconstituted to various final concentrations e.g. SIMULECT™ is reconstituted to a concentration of 4 mg/ml antibody, REMICADE™ is reconstituted to a concentration of 10 mg/ml, HERCEPTIN™ to 21 mg/ml, SYNAGIS™ and RAPTIVA™ to 100 mg/ml, and XOLAIR™ to 125 mg/ml.

Pre-Lyophilisates, Lyophilisates and Aqueous Reconstitution

Before a lyophilisate can be administered to a patient it should be reconstituted with an aqueous reconstituent. This step permits antibody and other components in the lyophilisate to re-dissolve to give a solution which is suitable for injection to a patient.

The volume of aqueous material used for reconstitution dictates the concentration of the antibody in a resulting pharmaceutical composition. Reconstitution with a smaller volume of reconstituent than the pre-lyophilisation volume provides a composition which is more concentrated than before lyophilisation. The reconstitution factor (volume of formulation after lyophilisation:volume of formulation before) may be from 1:0.5 to 1:6. A reconstitution factor of 1:3 is useful. As mentioned above, lyophilisates of the invention can be reconstituted to give aqueous compositions with an anti-CD40 antibody concentration of at least 50 mg/ml, 100 mg/ml, 150 mg/ml. 200 mg/ml, 250 mg/ml or 300 mg/ml, and the volume of reconstituent will be selected accordingly. If required, the reconstituted formulation can be diluted prior to administration to a patient as appropriate to deliver the intended dose.

Typical reconstituents for lyophilised antibodies include sterile water or buffer, optionally containing a preservative. If the lyophilisate includes a buffering agent then the reconstituent may include further buffering agent (which may be the same as or different from the lyophilisate's buffering agent) or it may instead include no buffering agent (e.g. WFI (water for injection), or physiological saline).

When present, components (i) to (iv) will be at a pre-lyophilisation concentration sufficient to maintain the anti-CD40 antibody in a form which is active and soluble after storage (under normal conditions) and reconstitution. The components will also be present after reconstitution.

Thus a sugar, such as sucrose or trehalose, may be present before lyophilisation at a concentration of between 3 and 300 mM e.g. 15-200 mM, 30-150 mM, 80-100 mM. A concentration of 90 mM sucrose is useful. A buffering agent, such as histidine, may be present before lyophilisation at a concentration of between 1 and 60 mM e.g. 3-30 mM, 5-20 mM, 5-15 mM. A concentration of 10 mM histidine buffer is useful. A surfactant, such as polysorbate 80 or polysorbate 20 may be present before lyophilisation at a concentration of up to 0.2% (by volume) e.g. 0.01-0.1%, 0.01-0.08%, 0.01-0.04%. A concentration of 0.02% polysorbate 80 or polysorbate 20 is useful. A free amino acid, such as arginine, methionine or glycine, may be present before lyophilisation at a concentration of between 2 and 80 mM e.g. 3-60 mM, 3-50 mM, 6-30 mM, 10-25 mM, 15-20 mM. A concentration of 17 mM arginine-HCl or 20 mM glycine-HCl or 60 mM methionine is useful. The anti-CD40 antibody is present before lyophilisation at a concentration of between 20 mg/ml and 120 mg/ml, e.g. 20 mg/ml, 30 mg/ml, 40 mg/ml, 50 mg/ml, 60 mg/ml, 66.6 mg/ml, 70 mg/ml, 80 mg/ml, 90 mg/ml, 100 mg/ml, 110 mg/ml, or 120 mg/ml. A concentration of 50 mg/ml is useful.

The pre-lyophilisate of the invention has a pH between 5.0 and 8.0, between 5.0 and 7.0, between 5.5 and 6.5. In a specific embodiment, the pre-lyophilisate of the invention has a pH of about 6.0.

In one embodiment the pre-lyophilisate of the invention has a molar ratio of sucrose:antibody of 90:1 and a molar ratio of histidine:antibody of 10:1.

In one embodiment the pre-lyophilisate of the invention has a molar ratio of sucrose:antibody of 90:1, a molar ratio of histidine:antibody of 10:1, and a molar ratio of arginine-HCl:antibody of 17:1.

In one embodiment the pre-lyophilisate of the invention has a molar ratio of sucrose:antibody of 90:1, a molar ratio of histidine:antibody of 10:1, and a molar ratio of glycine-HCl:antibody of 60:1.

A formulation containing histidine buffer, sucrose, polysorbate 20 and, optionally arginine, methionine or glycine has been shown to be suitable for lyophilisation of antibody mAb1. After reconstitution, the components of the lyophilisate may be present at a concentration of the aqueous pharmaceutical compositions as described hereinbefore.

Target Diseases and Disorders

The aqueous pharmaceutical compositions of the invention comprising anti-CD40 antibodies can be used to treat, ameliorate or prevent CD40-related autoimmune disorders, CD40-related inflammatory disorders and/or to prevent or reduce the risk of graft rejection in transplantation. For the purposes of the present invention, the term "inflammatory disorders" includes "autoimmune disorders".

As used herein, the term "autoimmunity" is generally understood to encompass inflammatory immune-mediated processes involving "self" antigens. In autoimmune diseases, self antigen(s) trigger host immune responses.

Pharmaceutical compositions comprising anti-CD40 antibodies are particularly useful to treat Multiple Sclerosis, Systemic Lupus Erythematosus, Sjögren's syndrome, Rheumatoid Arthritis, transplant rejection; graft-versus-host disease, Pemphigus vulgaris; and B cell neoplasms such as acute lymphoblastic leukemia (ALL) and B-cell chronic lymphocytic leukemia (CLL).

Also, the present invention includes treatment of inflammation associated with tissue transplant rejection. "Transplant rejection" or "graft rejection" refers to any host-mounted immune response against a graft including but not limited to HLA antigens, blood group antigens, and the like.

The invention can also be used to treat graft versus host disease, such as that associated with bone marrow transplantation, for example. In such graft versus host disease, the donor bone marrow includes lymphocytes and cells that mature into lymphocytes. The donor's lymphocytes recognise the recipient's antigens as non-self and mount an inflammatory immune response. Hence, as used herein, "graft versus host disease" or "graft versus host reaction" refers to any T cell mediated immune response in which donor lymphocytes react to the host's antigens.

The antagonist anti-CD40 antibodies or proteins described herein, for example mAb1, mAb2 or mAb3, can be used in accordance with the methods of the invention to treat autoimmune and/or inflammatory disorders including, but not limited to, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), primary Sjögren's syndrome (pSS), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue, immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1, 2, 3, and 4 delayed-type hypersensitivity, allergy or allergic disorders, unwanted/unintended immune responses to therapeutic proteins (see for example, U. S. Patent Application No. US 2002/0119151 and Koren, et al. (2002) Curr. Pharm. Biotechnol. 3: 349-60), asthma, Churg-Strauss syndrome (allergic granulomatosis), atopic dermatitis, allergic and irritant contact dermatitis, urtecaria, IgE-mediated allergy, atherosclerosis, ANCA-associated Vasculitides, vasculitis, idiopathic inflammatory myopathies, hemolytic disease, Alzheimer's disease, chronic inflammatory demyelinating polyneuropathy, and the like.

Genetic ablation or pharmacological inhibition of the CD40-CD154 pathway has previously demonstrated therapeutic benefit in either the clinic or in preclinical models of SLE, pSS, ITP, MS, Crohn's disease, Pemphigus vulgaris, autoimmune vasculitis and RA (Law C L, Grewal I S. (2009). Adv. Exp. Med. Biol. 2009; 647:8-36); the medical need of which is detailed below.

In preferred embodiments the anti-CD40 antibodies or proteins of the invention are useful in treating: (i) systemic lupus erythematosus (lupus nephritis), preferably in providing effective steroid-sparing therapies for induction and maintenance of remission, and prevention of end-stage renal disease; (ii) primary Sjögren's syndrome, preferably in prevention of salivary and lacrimary gland destruction, and induction and maintenance of remission of extraglandular manifestations; (iii) autoimmune thrombocytopenic purpura, preferably treatment of patients refractory to standard of care; (iv) ANCA-associated Vasculitides, preferably inducing and maintaining remission in patients refractory to corticosteroids, and steroid-sparing treatment; (v) Pemphigus Vulgaris, preferably in induction and maintenance of remission in patients refractory to corticosteroids, and steroid-sparing treatment; (vi) Multiple Sclerosis, preferably in providing more effective treatments for prevention of relapses and disability progression, and achieving disease-free status; and (vii) Crohn's disease, preferably in providing more effective therapies for maintenance of remission, and treatment of patients refractory to anti-TNF.

In some other embodiments, the anti-CD40 antibodies or proteins of the invention are useful in treating pulmonary inflammation including but not limited to lung graft rejection, asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, bronchiolitis obliterans due to bone marrow and/or lung transplantation or other causes, graft atherosclerosis/graft phlebosclerosis, as well as pulmonary fibrosis resulting from collagen, vascular, and autoimmune diseases such as rheumatoid arthritis, scleroderma and lupus erythematosus.

"Treatment" is herein defined as the application or administration of an anti-CD40 antibody or protein according to the invention, for example, mAb1, mAb2 or mAb3 antibody, to a subject, or application or administration a pharmaceutical composition comprising said anti-CD40 antibody or protein of the invention to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to cure, heal, alleviate, relieve, alter, remedy, ameliorate, improve, or affect the autoimmune disease and/or inflammatory disease, any associated symptoms of the autoimmune disease and/or inflammatory disease, or the predisposition toward the development of the autoimmune disease and/or inflammatory disease.

By "treatment" is also intended the application or administration of a pharmaceutical composition comprising an anti-CD40 antibodies or protein of the invention, for example, mAb1, mAb2 or mAb3 antibody, to a subject, or application or administration of a pharmaceutical composition comprising said anti-CD40 antibody or protein of the invention to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to cure, heal, alleviate, relieve, alter, remedy, ameliorate, improve, or affect the autoimmune disease and/or inflammatory disease, any associated symptoms of the autoimmune disease and/or inflammatory disease, or the predisposition toward the development of the autoimmune disease and/or inflammatory disease.

By "anti-inflammatory activity" is intended a reduction or prevention of inflammation. Therapy with at least one anti-CD40 antibody or protein according to the invention causes a physiological response that is beneficial with respect to treatment of an autoimmune disease and/or inflammatory disease, where the disease involves cells expressing the CD40 antigen. It is recognised that the methods of the invention may be useful in preventing phenotypic change in cells such as proliferation, activation, and the like.

Patient Administration

A pharmaceutical composition of the invention can be administered to a patient. Administration will typically be via a syringe. Thus the invention provides a delivery device (e.g. a syringe) including a pharmaceutical composition of the invention (e.g., pre-filled syringe). Patients will receive an effective amount of the anti-CD40 antibody as the principal active ingredient i.e. an amount that is sufficient to treat, ameliorate, or prevent the disease or disorder in question. Therapeutic effects may also include reduction in physical symptoms. The optimum effective amount and concentration of antibody for any particular subject will depend upon various factors, including the patient's age size health and/or gender, the nature and extent of the condition, the activity of the particular antibody, the rate of its clearance by the body, and also on any possible further therapeutic(s) administered in combination with the antibody. The effective amount delivered for a given situation can be determined within the judgment of a clinician. For purposes of the present invention, an effective dose may be from about 0.005 mg/kg to about 50 mg/kg, or about 0.05 mg/kg to about 10 mg/kg. Known antibody-based pharmaceuticals provide guidance in this respect e.g. HERCEPTIN™ is administered with an initial loading dose of 4 mg/kg body weight and a weekly maintenance dose of 2 mg/kg body weight; RITUXAN™ is administered weekly at 375 mg/m²; SYNAGIS™ is administered intramuscularly at 15 mg/kg body weight; etc.

The invention provides a method for delivering a monoclonal antibody to a mammal, comprising a step of administering to the patient a pharmaceutical composition of the invention.

The invention also provides a method for delivering a monoclonal antibody to a mammal, comprising steps of: (i) reconstituting a lyophilisate of the invention to give an aqueous formulation, and (ii) administering the aqueous formulation to the patient. Step (ii) ideally takes place within 24 hours of step (i) e.g. within 12 hours, within 6 hours, within 3 hours, or within 1 hour.

The invention also provides formulations of the invention for use as medicaments e.g. for use in delivering an antibody to a mammal, or for use in treating, preventing or ameliorating one or more of the diseases and disorders described above.

The mammal is preferably a human but may also be, for example, a horse or a cow or a dog or a cat. The antibodies will ideally be chosen to match the target species e.g. a human antibody for human administration, an equine antibody for horses, a canine antibody for dogs, etc. If native host antibodies are not available then transfer of antibody specificity from one species to another can be achieved by transfer of CDR residues (and typically, in addition, one or more framework residues) from a donor antibody into a recipient framework from the host species e.g. as in humanisation. Equinised, bovinised, caninised and felinised antibodies are known in the art. The antibody will bind to CD40 from the target species, but it may also cross-react with CD40 from other species.

Dosage can be by a single dose schedule or a multiple dose schedule.

Ingredients for forming compositions of the invention (e.g. lyophilisates and reconstituents) may be supplied in hermetically-sealed containers.

The Anti-CD40 Antibody

The invention concerns the formulation of anti-CD40 antibodies and more specifically the antibodies designated mAb1, mAb2, and mAb3, especially mAb1.

One suitable antibody that can be comprised in the pharmaceutical compositions of the invention is the human recombinant antibody mAb1, structurally characterised as further described below. The $V_H$ amino acid sequence of such isolated anti-CD40 antibody is shown in SEQ ID NO: 1. The $V_L$ amino acid sequence of such isolated anti-CD40 antibody is shown in SEQ ID NO: 2. The full length heavy chain amino acid sequence of such isolated anti-CD40 antibody is shown in SEQ ID NO: 9. The full-length light chain amino acid sequence of such isolated anti-CD40 antibody is shown in SEQ ID NO: 10. Another example of heavy and light chain amino acid sequences of such isolated anti-CD40 antibodies are those encoded by the nucleotide sequences of SEQ ID NO: 11 and SEQ ID NO: 12 respectively.

Other anti-CD40 antibodies that can be used for preparing the pharmaceutical compositions of the invention include anti-CD40 antibodies with amino acids that have been mutated by amino acid deletion, insertion or substitution, yet have no more than 1, 2, 3, 4 or 5 amino acid deletions, insertions or substitutions in either the heavy or light chain regions described above. In a specific embodiment, such amino acid changes appear only within the framework and/or constant regions and the CDR regions are 100% identical to the heavy chain CDR1, CDR2 and CDR3 regions of SEQ ID NO: 3, 4 and 5 and to the light chain CDR1, CDR2 and CDR3 regions of SEQ ID NO: 6, 7, and 8 respectively. In one more specific embodiment, the changes that have been made are only conservative amino acid substitutions outside of the CDR regions.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues outside of the CDR regions of an anti-CD40 antibody, can be replaced with other amino acid residues from the same side chain family, and the altered antibody can be tested for retained function, in particular the same binding properties to CD40.

Antibodies may typically be glycosylated. N-linked glycans attached to the $C_H2$ domain of a heavy chain, for instance, can influence C1q and FcR binding, and aglycosylated antibodies (for example comprising an N297A mutation) may have lower or different affinity for these receptors. The glycan structure can also affect activity e.g. differences in complement-mediated cell death may be seen depending on the number of galactose sugars (0, 1 or 2) at the terminus of a glycan's biantennary chain. An antibody's glycans preferably do not lead to a human immunogenic response after administration.

Another modification of the anti-CD40 antibodies herein that is contemplated by the invention is pegylation. An antibody can be pegylated to, for example, increase the biological (e.g., serum) half-life of the antibody. To pegylate an antibody, the antibody, or fragment thereof, typically may be reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer).

As used herein, the term "polyethylene glycol" is intended to encompass any of the forms of PEG that have been used to derivatise other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Any other natural or non-natural post-translational modification of anti-CD40 antibodies (e.g. mAb1) is further contemplated as specific embodiments of anti-CD40 antibodies that could be used for preparing the pharmaceutical compositions of the invention.

Antibodies can be prepared in a form free from products with which they would naturally be associated. Contaminant components of an antibody's natural environment include materials such as enzymes, hormones, or other host cell proteins.

The various features and embodiments of the present invention, referred to in individual sections and embodiments above apply, as appropriate, to other sections and embodiments, mutatis mutandis. Consequently features specified in one section or embodiment may be combined with features specified in other sections or embodiments, as appropriate.

EXAMPLES

Preparing Anti-CD40 Antibodies

CHIR-12.12, and mAb1 (N297A CHIR-12.12), mAb2 (D265A CHIR-12.12), and mAb3 (CHIR-12.12 LALA) bind specifically to CD40. Tables 1 and 2 below summarise the sequence characteristics of these antibodies. These antibodies may be produced in mammalian host cells, such as, a CHO cell line transfected with expression vectors carrying heavy and light chain coding sequences under suitable expression promoters.

TABLE 1

Brief description of the sequences listed in the sequence listing of Table 2

| SEQ ID NO: | Description of the sequence |
|---|---|
| 1 | Amino acid sequence of the variable region ($V_H$) of the heavy chain of CHIR-12.12, mAb1, mAb2 and mAb3 |
| 2 | Amino acid sequence of the variable region ($V_L$) of the light chain of CHIR-12.12, mAb1, mAb2 and mAb3 |
| 3 | Amino acid sequence of HCDR1 of CHIR-12.12, mAb1, mAb2 and mAb3 |
| 4 | Amino acid sequence of HCDR2 of CHIR-12.12, mAb1, mAb2 and mAb3 |
| 5 | Amino acid sequence of HCDR3 of CHIR-12.12, mAb1, mAb2 and mAb3 |
| 6 | Amino acid sequence of LCDR1 of CHIR-12.12, mAb1, mAb2 and mAb3 |
| 7 | Amino acid sequence of LCDR2 of CHIR-12.12, mAb1, mAb2 and mAb3 |
| 8 | Amino acid sequence of LCDR3 of CHIR-12.12, mAb1, mAb2 and mAb3 |
| 9 | Amino acid sequence of the full length heavy chain of mAb1 |
| 10 | Amino acid sequence of the full length light chain of mAb1 |
| 11 | Nucleotide sequence encoding full length heavy chain of mAb1 (SEQ ID NO: 9) |
| 12 | Nucleotide sequence encoding full length light chain of mAb1 (SEQ ID NO: 10) |
| 13 | Amino acid sequence of the full length heavy chain of mAb2 |
| 14 | Amino acid sequence of the full length light chain of mAb2 |
| 15 | Nucleotide sequence encoding full length heavy chain of mAb2 (SEQ ID NO: 13) |
| 16 | Nucleotide sequence encoding full length light chain of mAb2 (SEQ ID NO: 14) |
| 17 | Amino acid sequence of the full length heavy chain of mAb3 |
| 18 | Amino acid sequence of the full length light chain of mAb3 |
| 19 | Nucleotide sequence encoding full length heavy chain of mAb3 (SEQ ID NO: 17) |
| 20 | Nucleotide sequence encoding full length light chain of mAb3 (SEQ ID NO: 18) |
| 21 | Amino acid sequence of human CD40 |

TABLE 2

Sequence listing

| SEQ ID NO: | Amino acid or Nucleotide Sequence |
|---|---|
| 1 | QVQLVESGGGVVQPGRSLRLSCAASGFTFSSYGMHWVRQAPGKGLEWVAV ISYEESNRYHADSVKGRFTISRDNSKITLYLQMNSLRTEDTAVYYCARDGGIA APGPDYWGQGTLVTVSS |
| 2 | DIVMTQSPLSLTVTPGEPASISCRSSQSLLYSNGYNYLDWYLQKPGQSPQVLI SLGSNRASGVPDRFSGSGSGTDFTLKISRVEAEDVGVYYCMQARQTPFTFG PGTKVDIR |
| 3 | SYGMH |
| 4 | VISYEESNRYHADSVKG |
| 5 | DGGIAAPGPDY |
| 6 | RSSQSLLYSNGYNYLD |
| 7 | LGSNRAS |
| 8 | MQARQTPFT |
| 9 | QVQLVESGGGVVQPGRSLRLSCAASGFTFSSYGMHWVRQAPGKGLEWVAV ISYEESNRYHADSVKGRFTISRDNSKITLYLQMNSLRTEDTAVYYCARDGGIA APGPDYWGQGTLVTVSSASTKGPSVFPLAPSSKSTSGGTAALGCLVKDYFP |

TABLE 2-continued

Sequence listing

| SEQ ID NO: | Amino acid or Nucleotide Sequence |
|---|---|
|  | EPVTVSWNSGALTSGVHTFPAVLQSSGLYSLSSVVTVPSSSLGTQTYICNVN<br>HKPSNTKVDKRVEPKSCDKTHTCPPCPAPELLGGPSVFLFPPKPKDTLMISR<br>TPEVTCVVVDVSHEDPEVKFNWYVDGVEVHNAKTKPREEQYASTYRVVSVL<br>TVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLY<br>SKLTVDKSRWQQGNVFSCSVMHEALHNHYTQKSLSLSPGK |
| 10 | DIVMTQSPLSLTVTPGEPASISCRSSQSLLYSNGYNYLDWYLQKPGQSPQVLI<br>SLGSNRASGVPDRFSGSGSGTDFTLKISRVEAEDVGVYYCMQARQTPFTFG<br>PGTKVDIRRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGLSS<br>PVTKSFNRGEC |
| 11 | CAGGTGCAGCTGGTGGAATCTGGCGGCGGAGTGGTGCAGCCTGGCCGG<br>TCCCTGAGACTGTCTTGCGCCGCCTCCGGCTTCACCTTCTCCAGCTACGG<br>CATGCACTGGGTGCGACAGGCCCCTGGCAAGGGACTGGAATGGGTGGC<br>CGTGATCTCCTACGAGGAATCCAACAGATACCACGCTGACTCCGTGAAGG<br>GCCGGTTCACAATCTCCCGGGACAACTCCAAGATCACCCTGTACCTGCAG<br>ATGAACTCCCTGCGGACCGAGGACACCGCCGTGTACTACTGCGCCAGGG<br>ACGGAGGAATCGCCGCTCCTGGACCTGATTATTGGGGCCAGGGCACCCT<br>GGTGACAGTGTCCTCCGCTAGCACCAAGGGCCCCTCCGTGTTCCCTCTG<br>GCCCCCTCCAGCAAGTCCACCTCTGGCGGCACCGCCGCTCTGGGCTGCC<br>TGGTGAAAGACTACTTCCCCGAGCCCGTGACCGTGTCCTGGAACTCTGG<br>CGCCCTGACCTCCGGCGTGCACACCTTTCCAGCCGTGCTGCAGTCCTCC<br>GGCCTGTACTCCCTGTCCTCCGTGGTGACCGTGCCCTCTAGCTCTCTGG<br>GCACCCAGACCTACATCTGCAACGTGAACCACAAGCCCTCCAACACCAAG<br>GTGGACAAGCGGGTGGAACCCAAGTCCTGCGACAAGACCCACACCTGTC<br>CCCCCTGCCCTGCCCCTGAACTGCTGGGCGGACCTTCCGTGTTCCTGTT<br>CCCCCCAAAGCCCAAGGACACCCTGATGATCTCCCGGACCCCCGAAGTG<br>ACCTGCGTGGTGGTGGACGTGTCCCACGAGGACCCTGAAGTGAAGTTCA<br>ATTGGTACGTGGACGGCGTGGAAGTGCACAACGCCAAGACCAAGCCCAG<br>AGAGGAACAGTACGCCTCCACCTACCGGGTGGTGTCTGTGCTGACCGTG<br>CTGCACCAGGACTGGCTGAACGGCAAAGAGTACAAGTGCAAGGTCTCCA<br>ACAAGGCCCTGCCTGCCCCCATCGAAAAGACCATCTCCAAGGCCAAGGG<br>CCAGCCCCGCGAGCCACAGGTGTACACACTGCCCCCCAGCCGGGAAGA<br>GATGACCAAGAACCAGGTGTCCCTGACCTGTCTGGTCAAAGGCTTCTACC<br>CCTCCGATATCGCCGTGGAGTGGGAGTCCAACGGACAGCCCGAGAACAA<br>CTACAAGACCACCCCCCCTGTGCTGGACTCCGACGGCTCATTCTTCCTGT<br>ACTCCAAGCTGACCGTGGACAAGTCCCGGTGGCAGCAGGGCAACGTGTT<br>CTCCTGCTCCGTGATGCACGAGGCCCTGCACAACCACTACACCCAGAAG<br>TCCCTGTCCCTGAGCCCCGGCAAG |
| 12 | GACATCGTGATGACCCAGTCCCCCCTGTCCCTGACCGTGACACCTGGCG<br>AGCCTGCCTCTATCTCCTGCAGATCCTCCCAGTCCCTGCTGTACTCCAAC<br>GGCTACAACTACCTGGACTGGTATCTGCAGAAGCCCGGCCAGTCCCCAC<br>AGGTGCTGATCTCCCTGGGCTCCAACAGAGCCTCTGGCGTGCCCGACCG<br>GTTCTCCGGCTCTGGCTCTGGCACCGACTTCACACTGAAGATCTCCACGGG<br>TGGAAGCCGAGGACGTGGGCGTGTACTACTGCATGCAGGCCCGGCAGA<br>CCCCCCTTCACCTTCGGCCCTGGCACCAAGGTGGACATCCGGCGTACGGT<br>GGCCGCTCCCAGCGTGTTCATCTTCCCCCCCAGCGACGAGCAGCTGAAG<br>AGCGGCACCGCCAGCGTGGTGTGCCTGCTGAACAACTTCTACCCCCGGG<br>AGGCCAAGGTGCAGTGGAAGGTGGACAACGCCCTGCAGAGCGGCAACA<br>GCCAGGAGAGCGTCACCGAGCAGGACAGCAAGGACTCCACCTACAGCCT<br>GAGCAGCACCCTGACCCTGAGCAAGGCCGACTACGAGAAGCATAAGGTG<br>TACGCCTGCGAGGTGACCCACCAGGGCCTGTCCAGCCCCGTGACCAAGA<br>GCTTCAACAGGGGCGAGTGC |
| 13 | QVQLVESGGGVVQPGRSLRLSCAASGFTFSSYGMHWVRQAPGKGLEWVAV<br>ISYEESNRYHADSVKGRFTISRDNSKITLYLQMNSLRTEDTAVYYCARDGGIA<br>APGPDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNVN<br>HKPSNTKVDKRVEPKSCDKTHTCPPCPAPELLGGPSVFLFPPKPKDTLMISR<br>TPEVTCVVVAVSHEDPEVKFNWYVDGVEVHNAKTKPREEQYNSTYRVVSVL<br>TVLHQDWLNGKEYKCKVSNKALPAPIEKTISKAKGQPREPQVYTLPPSREEM<br>TKNQVSLTCLVKGFYPSDIAVEWESNGQPENNYKTTPPVLDSDGSFFLYSKL<br>TVDKSRWQQGNVFSCSVMHEALHNHYTQKSLSLSPGK |
| 14 | DIVMTQSPLSLTVTPGEPASISCRSSQSLLYSNGYNYLDWYLQKPGQSPQVLI<br>SLGSNRASGVPDRFSGSGSGTDFTLKISRVEAEDVGVYYCMQARQTPFTFG<br>PGTKVDIRRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGLSS<br>PVTKSFNRGEC |
| 15 | CAGGTGCAGCTGGTGGAATCTGGCGGCGGAGTGGTGCAGCCTGGCCGG<br>TCCCTGAGACTGTCTTGCGCCGCCTCCGGCTTCACCTTCTCCAGCTACGG |

TABLE 2-continued

Sequence listing

| SEQ ID NO: | Amino acid or Nucleotide Sequence |
|---|---|
| | CATGCACTGGGTGCGACAGGCCCCTGGCAAGGGACTGGAATGGGTGGC<br>CGTGATCTCCTACGAGGAATCCAACAGATACCACGCTGACTCCGTGAAGG<br>GCCGGTTCACAATCTCCCGGGACAACTCCAAGATCACCCTGTACCTGCAG<br>ATGAACTCCCTGCGGACCGAGGACACCGCCGTGTACTACTGCGCCAGGG<br>ACGGAGGAATCGCCGCTCCTGGACCTGATTATTGGGGCCAGGGCACCCT<br>GGTGACAGTGTCCTCCGCTAGCACCAAGGGCCCCTCCGTGTTCCCTCTG<br>GCCCCCTCCAGCAAGTCCACCTCTGGCGGCACCGCCGCTCTGGGCTGCC<br>TGGTGAAAGACTACTTCCCCGAGCCCGTGACCGTGTCCTGGAACTCTGG<br>CGCCCTGACCTCCGGCGTGCACACCTTTCCAGCCGTGCTGCAGTCCTCC<br>GGCCTGTACTCCCTGTCCTCCGTGGTGACCGTGCCCTCTAGCTCTCTGG<br>GCACCCAGACCTACATCTGCAACGTGAACCACAAGCCCTCCAACACCAAG<br>GTGGACAAGCGGGTGGAACCCAAGTCCTGCGACAAGACCCACACCTGTC<br>CCCCCTGCCCTGCCCCTGAACTGCTGGGCGGACCTTCCGTGTTCCTGTT<br>CCCCCCAAAGCCCAAGGACACCCTGATGATCTCCCGGACCCCCGAAGTG<br>ACCTGCGTGGTGGTGGACGTGTCCCACGAGGACCCTGAAGTGAAGTTCA<br>ATTGGTACGTGGACGGCGTGGAAGTGCACAACGCCAAGACCAAGCCCAG<br>AGAGGAACAGTACAACTCCACCTACCGGGTGGTGTCTGTGCTGACCGTG<br>CTGCACCAGGACTGGCTGAACGGCAAGGAGTACAAGTGCAAGGTCTCCA<br>ACAAGGCCCTGCCTGCCCCCATCGAAAAGACCATCTCCAAGGCCAAGGG<br>CCAGCCCCGCGAGCCACAGGTGTACACACTGCCCCCCAGCCGGGAAGA<br>GATGACCAAGAACCAGGTGTCCCTGACCTGTCTGGTCAAAGGCTTCTACC<br>CCTCCGATATCGCCGTGGAGTGGGAGTCCAACGGACAGCCCGAGAACAA<br>CTACAAGACCACCCCCCCTGTGCTGGACTCCGACGGCTCATTCTTCCTGT<br>ACTCCAAGCTGACCGTGGACAAGTCCCGGTGGCAGCAGGGCAACGTGTT<br>CTCCTGCTCCGTGATGCACGAGGCCCTGCACAACCACTACACCCAGAAG<br>TCCCTGTCCCTGAGCCCCGGCAAG |
| 16 | GACATCGTGATGACCCAGTCCCCCCTGTCCCTGACCGTGACACCTGGCG<br>AGCCTGCCTCTATCTCCTGCAGATCCTCCCAGTCCCTGCTGTACTCCAAC<br>GGCTACAACTACCTGGACTGGTATCTGCAGAAGCCCGGCCAGTCCCCAC<br>AGGTGCTGATCTCCCTGGGCTCCAACAGAGCCTCTGGCGTGCCCGACCG<br>GTTCTCCGGCTCTGGCTCTGGCACCGACTTCACACTGAAGATCTCACGGG<br>TGGAAGCCGAGGACGTGGGCGTGTACTACTGCATGCAGGCCCGGCAGA<br>CCCCCTTCACCTTCGGCCCTGGCACCAAGGTGGACATCCGGCGTACGGT<br>GGCCGCTCCCAGCGTGTTCATCTTCCCCCCCAGCGACGAGCAGCTGAAG<br>AGCGGCACCGCCAGCGTGGTGTGCCTGCTGAACAACTTCTACCCCCGGG<br>AGGCCAAGGTGCAGTGGAAGGTGGACAACGCCCTGCAGAGCGGCAACA<br>GCCAGGAGAGCGTCACCGAGCAGGACAGCAAGGACTCCACCTACAGCCT<br>GAGCAGCACCCTGACCCTGAGCAAGGCCGACTACGAGAAGCATAAGGTG<br>TACGCCTGCGAGGTGACCCACCAGGGCCTGTCCAGCCCCGTGACCAAGA<br>GCTTCAACAGGGGCGAGTGC |
| 17 | QVQLVESGGGVVQPGRSLRLSCAASGFTFSSYGMHWVRQAPGKGLEWVAV<br>ISYEESNRYHADSVKGRFTISRDNSKITLYLQMNSLRTEDTAVYYCARDGGIA<br>APGPDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNVN<br>HKPSNTKVDKRVEPKSCDKTHTCPPCPAPEAAGGPSVFLFPPKPKDTLMISR<br>TPEVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSK<br>LTVDKSRWQQGNVFSCSVMHEALHNHYTQKSLSLSPGK |
| 18 | DIVMTQSPLSLTVTPGEPASISCRSSQSLLYSNGYNYLDWYLQKPGQSPQVLI<br>SLGSNRASGVPDRFSGSGSGTDFTLKISRVEAEDVGVYYCMQARQTPFTFG<br>PGTKVDIRRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGLSS<br>PVTKSFNRGEC |
| 19 | CAGGTGCAGCTGGTGGAATCTGGCGGCGGAGTGGTGCAGCCTGGCCGG<br>TCCCTGAGACTGTCTTGCGCCGCCTCCGGCTTCACCTTCTCCAGCTACGG<br>CATGCACTGGGTGCGACAGGCCCCTGGCAAGGGACTGGAATGGGTGGC<br>CGTGATCTCCTACGAGGAATCCAACAGATACCACGCTGACTCCGTGAAGG<br>GCCGGTTCACAATCTCCCGGGACAACTCCAAGATCACCCTGTACCTGCAG<br>ATGAACTCCCTGCGGACCGAGGACACCGCCGTGTACTACTGCGCCAGGG<br>ACGGAGGAATCGCCGCTCCTGGACCTGATTATTGGGGCCAGGGCACCCT<br>GGTGACAGTGTCCTCCGCTAGCACCAAGGGCCCCTCCGTGTTCCCTCTG<br>GCCCCCTTCCAGCAAGTCTACCTCCGGCGGCACAGCTGCTCTGGGCTGCC<br>TGGTCAAGGACTACTTCCCTGAGCCTGTGACAGTGTCCTGGAACTCTGGC<br>GCCCTGACCTCGGCGTGCACACCTTCCCTGCCGTGCTGCAGTCCTCCG<br>GCCTGTACTCCCTGTCCTCCGTGGTCACAGTGCCTTCAAGCAGCCTGGG<br>CACCCAGACCTATATCTGCAACGTGAACCACAAGCCTTCCAACACCAAGG<br>TGGACAAGCGGGTGGAGCTAAGTCCTGCGACAAGACCCACACCTGTCC<br>TCCCTGCCCTGCTCCTGAAGCTGCTGGCGGCCCTTCTGTGTTCCTGTTCC<br>CTCCAAAGCCCAAGGACACCCTGATGATCTCCCGGACCCCTGAAGTGAC<br>CTGCGTGGTGGTGGACGTGTCCCACGAGGATCCTGAAGTGAAGTTCAATT |

TABLE 2-continued

Sequence listing

| SEQ ID NO: | Amino acid or Nucleotide Sequence |
|---|---|
|  | GGTACGTGGACGGCGTGGAGGTGCACAACGCCAAGACCAAGCCTCGGG<br>AGGAACAGTACAACTCCACCTACCGGGTGGTGTCCGTGCTGACCGTGCT<br>GCACCAGGACTGGCTGAACGGCAAAGAGTACAAGTGCAAAGTCTCCAAC<br>AAGGCCCTGCCTGCCCCTATCGAAAAGACAATCTCCAAGGCCAAGGGCC<br>AGCCTAGGGAACCCCAGGTGTACACCCTGCCACCCAGCCGGGAGGAAAT<br>GACCAAGAACCAGGTGTCCCTGACCTGTCTGGTCAAGGGCTTCTACCCTT<br>CCGATATCGCCGTGGAGTGGGAGTCTAACGGCCAGCCTGAGAACAACTA<br>CAAGACCACCCCTCCTGTGCTGGACTCCGACGGCTCCTTCTTCCTGTACT<br>CCAAACTGACCGTGGACAAGTCCCGGTGGCAGCAGGGCAACGTGTTCTC<br>CTGCTCCGTGATGCACGAGGCCCTGCACAACCACTACACCCAGAAGTCC<br>CTGTCCCTGTCTCCCGGCAAG |
| 20 | GACATCGTGATGACCCAGTCCCCCCTGTCCCTGACCGTGACACCTGGCG<br>AGCCTGCCTCTATCTCCTGCAGATCCTCCCAGTCCCTGCTGTACTCCAAC<br>GGCTACAACTACCTGGACTGGTATCTGCAGAAGCCCGGCCAGTCCCCAC<br>AGGTGCTGATCTCCCTGGGCTCCAACAGAGCCTCTGGCGTGCCCGACCG<br>GTTCTCCGGCTCTGGCTCTGGCACCGACTTCACACTGAAGATCTCACGGG<br>TGGAAGCCGAGGACGTGGGCGTGTACTACTGCATGCAGGCCCGGCAGA<br>CCCCCTTCACCTTCGGCCCTGGCACCAAGGTGGACATCCGGCGTACGGT<br>GGCCGCTCCCAGCGTGTTCATCTTCCCCCCCAGCGACGAGCAGCTGAAG<br>AGCGGCACCGCCAGCGTGGTGTGCCTGCTGAACAACTTCTACCCCCGGG<br>AGGCCAAGGTGCAGTGGAAGGTGGACAACGCCCTGCAGAGCGGCAACA<br>GCCAGGAGAGCGTCACCGAGCAGGACAGCAAGGACTCCACCTACAGCCT<br>GAGCAGCACCCTGACCCTGAGCAAGGCCGACTACGAGAAGCATAAGGTG<br>TACGCCTGCGAGGTGACCCACCAGGGCCTGTCCAGCCCCGTGACCAAGA<br>GCTTCAACAGGGGCGAGTGC |
| 21 | MVRLPLQCVLWGCLLTAVHPEPPTACREKQYLINSQCCSLCQPGQKLVSDC<br>TEFTETECLPCGESEFLDTWNRETHCHQHKYCDPNLGLRVQQKGTSETDTIC<br>TCEEGWHCTSEACESCVLHRSCSPGFGVKQIATGVSDTICEPCPVGFFSNVS<br>SAFEKCHPWTSCETKDLVVQQAGTNKTDVVCGPQDRLRALVVIPIIFGILFAIL<br>LVLVFIKKVAKKPTNKAPHPKQEPQEINFPDDLPGSNTAAPVQETLHGCQPVT<br>QEDGKESRISVQERQ |

Examples of Formulations

A high concentration lyophilised or liquid formulation of mAb1 was desired and so formulation studies were performed. A lyophilised formulation comprising a sugar, a buffering agent and a surfactant was stable and could maintain high antibody concentrations after reconstitution.

Five formulations (F1, F2, F3, F4 and F5) of mAb1 were evaluated for stability. F1 was a liquid formulation at 50 mg/mL mAb1 at pH 6.0. Formulations F2, F3, F4, and F5 had prior to lyophilisation, 50 mg/vial mAb1. Formulations F2, F3, F4 and F5 had, prior to lyophilisation, 50 mg/ml mAb1 at pH 6.0. Formulations F2, F3, F4 and F5 had a fill volume of 3.6 ml. The five formulations included buffer, sugar, surfactant and free amino acid as listed in Table 3:

TABLE 3

Examples of formulations

|  | mAb1 | Histidine buffer | Stabiliser | Surfactant | Amino acid |
|---|---|---|---|---|---|
| F1 | 50 mg/ml | 10 mM | 190 mM trehalose | 0.02% polysorbate 20 | 40 mM arginine-HCl |
| F2 | 50 mg/ml | 10 mM | 90 mM trehalose | 0.02% polysorbate 20 | 17 mM arginine-HCl |
| F3 | 50 mg/ml | 10 mM | 90 mM sucrose | 0.02% polysorbate 20 | 17 mM arginine-HCl |
| F4 | 50 mg/ml | 10 mM | 90 mM trehalose | 0.02% polysorbate 20 | — |
| F5 | 50 mg/ml | 10 mM | 90 mM sucrose | 0.02% polysorbate 20 | — |

The F2, F3, F4, and F5 lyophilisates were reconstituted with WFI (1.0 ml) to give a reconstituted volume of 1.2 ml (⅓ the original aqueous volume). The reconstituted compositions were as listed in Table 4:

TABLE 4

Examples of formulations

|  | mAb1 | Histidine buffer | Stabiliser | Surfactant | Amino acid |
|---|---|---|---|---|---|
| F2 | 150 mg/ml | 30 mM histidine | 270 mM trehalose | 0.06% polysorbate 20 | 51 mM arginine-HCl |
| F3 | 150 mg/ml | 30 mM histidine | 270 mM sucrose | 0.06% polysorbate 20 | 51 mM arginine-HCl |
| F4 | 150 mg/ml | 30 mM histidine | 270 mM trehalose | 0.06% polysorbate 20 | — |
| F5 | 150 mg/ml | 30 mM histidine | 270 mM sucrose | 0.06% polysorbate 20 | — |

The lyophilisation cycle used is reported in Table 5.

TABLE 5

The lyophilisation cycle parameters

| Step | Operation | Time [hh:mm] | Shelf temp. | Chamber pressure |
|---|---|---|---|---|
| 1 | Vial loading | As required | 20° C. | Ambient |
| 2 | 5° C. cooling | 00:30 | 5° C. | Ambient |
| 3 | 5° C. hold | 03:00 | 5° C. | Ambient |
| 4 | Freeze ramp | 01:24 | 5° C. to −37° C. | Ambient |
| 5 | Freeze hold | 06:00 | −37° C. | Ambient |
| 6 | Chamber Vacuum | as required | −37° C. | 0.2 mbar[a] |

TABLE 5-continued

The lyophilisation cycle parameters

| Step | Operation | Time [hh:mm] | Shelf temp. | Chamber pressure |
|---|---|---|---|---|
| 7 | Primary drying ramp | 16:00 | −37° C. to 25° C. | 0.2 mbar[a] |
| 8 | Secondary drying hold | 24:00 | 25° C. | 0.2 mbar[a] |
| 11 | Vial stoppering | | 25° C. | 850 ± 50 mbar |

[a]Chamber pressure was controlled using sterile filtered nitrogen. The pressure was determined by instruments based on capacitance measurements.

The five formulations were tested for stability at various time points after formulation/reconstitution as listed below.

Size exclusion-High Pressure Liquid Chromatography (SEC-HPLC) was used to assess the amount of mAb1 in each formulation at the time of formulation (T0), 4 weeks (25° C.), 4 weeks (40° C.), 6 months (2-8° C.), 6 months (25° C.) and 6 months (40° C.). The amount of antibody is expressed as a percentage of the starting amount, as listed in Table 6. The F1 formulation remains close to 50 mg/ml±5 mg/ml (100%±10%), the F2, F3, F4 and F5 formulations remain close to 150 mg/ml±15 mg/ml (100%±10%).

TABLE 6

Amount of antibody from SEC-HPLC

| | T0 | 4 weeks (25° C.) | 4 weeks (40° C.) | 6 months (2-8° C.) | 6 months (25° C.) | 6 months (40° C.) |
|---|---|---|---|---|---|---|
| F1 | 100% ± 10% | 100% ± 10% | 100% ± 10% | 100% ± 10% | 100% ± 10% | 100% ± 10% |
| F2 | 100% ± 10% | — | 100% ± 10% | — | 100% ± 10% | 100% ± 10% |
| F3 | 100% ± 10% | — | 100% ± 10% | — | — | 100% ± 10% |
| F4 | 100% ± 10% | — | 100% ± 10% | — | 100% ± 10% | 100% ± 10% |
| F5 | 100% ± 10% | — | 100% ± 10% | — | 100% ± 10% | 100% ± 10% |

The potency of the mAb1 antibody in each formulation was measured by ELISA assay at T0, 4 weeks (25° C.), 4 weeks (40° C.), 6 months (2-8° C.), 6 months (25° C.) and 6 months (40° C.). The results, expressed as a percentage of the starting potency (100%) are listed in Table 7. The potency of the F1 formulation decreases with progression of time and increase of temperature; after 6 m at 40° C. potency was found to be 79%. The lowest value measured was 85% for F4 (6 m at 25° C.) and 86% for F3 (6 m at 40° C.)

TABLE 7

Potency of antibody as measured in ELISA

| | T0 | 4 weeks (25° C.) | 4 weeks (40° C.) | 6 months (2-8° C.) | 6 months (25° C.) | 6 months (40° C.) |
|---|---|---|---|---|---|---|
| F1 | 91.3 | 104.0 | 98.0 | 91.0 | 91.0 | 79.0 |
| F2 | 93.2 | | | | | |
| F3 | 95.7 | | | | | 86.0 |
| F4 | 96.5 | | | | 85.0 | 90.0 |
| F5 | 97.8 | | | | | |

Stability of the formulations was evaluated by % impurities as measured by size exclusion-High Pressure Liquid Chromatography (SEC-HPLC) and Dynamic Light Scattering (DLS). The results are shown in Tables 8 and 9.

TABLE 8

Aggregation products results from SEC-HPLC

| | T0 | 4 weeks (25° C.) | 4 weeks (40° C.) | 6 months (2-8° C.) | 6 months (25° C.) | 6 months (40° C.) |
|---|---|---|---|---|---|---|
| F1 | 0.26% | 0.26% | 0.59% | 0.38% | 0.47% | 2.76% |
| F2 | 0.38% | | 1.37% | | 1.40% | 3.80% |
| F3 | 0.29% | | 0.96% | | | 2.88% |
| F4 | 0.38% | | 1.94% | | 1.97% | 5.59% |
| F5 | 0.33% | | 1.32% | | 1.40% | 4.01% |

TABLE 9

Small particles; results for PolyDispensity Index (PDI) from Dynamic Light Scattering

| | T0 | 4 weeks (25° C.) | 4 weeks (40° C.) | 6 months (2-8° C.) | 6 months (25° C.) | 6 months (40° C.) |
|---|---|---|---|---|---|---|
| F1 | 52.8% | 30.2% | 39.3% | 41.3% | 52.9% | 59.9% |
| F2 | 48.8% | | 61.0% | | 44.4% | 46.6% |
| F3 | 50.4% | | 57.0% | | | 40.8% |
| F4 | 54.7% | | 61.8% | | 61.9% | 59.2% |
| F5 | 47.2% | | 60.0% | | 60.5% | 51.3% |

The F1 formulation showed an increase of aggregation products with increasing temperature and time. For the F2 to F5 formulations addition of arginine (F2 and F3) slightly reduced the level of aggregation; and sucrose (F3 and F5) was superior to trehalose.

Aggregation products were also evaluated by measuring turbidity. The F1 formulation showed an increase of turbidity with increase in temperature and with increase in time. The F2 to F5 formulations showed slightly increased turbidity values for formulations containing arginine (F2 and F3).

TABLE 10

Turbidity measurements (absorbance units)

| | T0 | 4 weeks (25° C.) | 4 weeks (40° C.) | 6 months (2-8° C.) | 6 months (25° C.) | 6 months (40° C.) |
|---|---|---|---|---|---|---|
| F1 | 7.38 | 11.30 | 12.90 | 9.7 | 12.7 | 17.9 |
| F2 | 9.36 | | 14.90 | | 12.1 | 11.3 |
| F3 | 8.98 | | 14.40 | | | 11.0 |
| F4 | 6.34 | | 10.40 | | 9.2 | 7.6 |
| F5 | 6.91 | | 10.70 | | 9.7 | 8.2 |

Stability of the formulations was evaluated by % degradation products as measured SEC-HPLC. With the F2 to F5 formulations the addition of arginine slightly reduced degradation. The results are shown in Table 11.

TABLE 11

Degradation products results from SEC-HPLC

|  | T0 | 4 weeks (25° C.) | 4 weeks (40° C.) | 6 months (2-8° C.) | 6 months (25° C.) | 6 months (40° C.) |
|---|---|---|---|---|---|---|
| F1 | 0.11% | 1.40% | 2.76% | 1.04% | 2.10% | 8.88% |
| F2 | 0.11% |  | 0.14% |  | 0.12% | 0.05% |
| F3 | 0.15% |  | 0.18% |  | 0.00% | 2.97% |
| F4 | 0.10% |  | 0.19% |  | 0.15% | 5.70% |
| F5 | 0.11% |  | 0.18% |  | 0.14% | 4.10% |

The four lyophilised formulations F2, F3, F4, and F5 were assessed for visual clarity after reconstitution. The results are presented in Table 12.

TABLE 12

Visual clarity

|  | T0 | 4 weeks (25° C.) | 4 weeks (40° C.) | 6 months (2-8° C.) | 6 months (25° C.) | 6 months (40° C.) |
|---|---|---|---|---|---|---|
| F2 | clear without particles | clear without particles | clear without particles | clear without particles | clear without particles | clear without particles |
| F3 | clear without particles | clear without particles | clear without particles | clear without particles | clear without particles | clear without particles |
| F4 | clear without particles | clear without particles | clear without particles | clear without particles | clear without particles | clear without particles |
| F5 | clear without particles | clear without particles | clear without particles | clear without particles | clear without particles | clear without particles |

The physico-chemical properties of the formulations were assessed; the results are presented in Table 13. The viscosity values are the values of the formulations having 50 mg/ml antibody prior to lyophilisation. The osmolality values correspond to the reconstituted compositions having 150 mg/ml antibody.

TABLE 13

Physico-chemical properties

|  | Viscosity mPa · s | Osmolality mOsm/kg |
|---|---|---|
| F1 | 2.1 | 318 |
| F2 | 1.7 | 580 |
| F3 | 1.6 | 556 |
| F4 | 1.6 | 461 |
| F5 | 1.6 | 443 |

CONCLUSIONS

Overall, the formulations tested showed good results. The bioassays (SEC and ELISA) showed that the formulations are comparable. Soluble aggregates were slightly reduced in the presence of arginine and were slightly lower for the sucrose containing formulations compared to the trehalose containing formulations. Turbidity was slightly increased in the presence of arginine; there was no difference between trehalose or sucrose containing formulations. Degradation was reduced in the presence of arginine. With regard to physico-chemical properties the pH, viscosity, residual moisture content, and visual aspects were comparable for all formulations. Osmolality was >300 mOsm/kg for all formulations, and was even higher in the presence of arginine-HCl (F2 and F3). It is desirable to have a formulation which is isotonic to plasma (290 mOsm/kg), or as close to this value as possible. The formulations having sucrose (F3 and F5) were considered preferable to those comprising trehalose. Whilst some beneficial effects on degradation were seen with arginine (F3), the lower osmolality of the F5 formulation was considered to be a more important factor. The F5 formulation was deemed to be the most optimal formulation.

The invention claimed is:

1. A lyophilised formulation prepared by lyophilising an aqueous formulation having a pH of 6.0 and comprising
   (i) an anti-CD40 antibody wherein the antibody has a concentration of 150 mg/ml, and wherein said anti-CD40 antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
   (ii) 270 mM sucrose as a stabiliser,
   (iii) 30 mM histidine as a buffering agent, and
   (iv) 0.06% polysorbate 20 as a surfactant.

2. An aqueous pharmaceutical composition obtained by reconstituting a lyophilised formulation of claim 1, wherein the reconstitution factor is between 1:0.5 to 1:6.

3. The aqueous pharmaceutical composition of claim 2, wherein the reconstitution factor is 1:3.

4. The lyophilised formulation of claim 1, wherein the anti-CD40 antibody comprises a $V_H$ domain having the amino acid sequence of SEQ ID NO: 1 and a $V_L$ domain having the amino acid sequence of SEQ ID NO: 2.

5. The lyophilised formulation of claim 1, wherein the anti-CD40 antibody comprises a heavy chain region of SEQ ID NO: 9 and a light chain region of SEQ ID NO: 10.

6. The lyophilised formulation of claim 1, wherein the anti-CD40 antibody comprises a heavy chain region of SEQ ID NO: 13 and a light chain region of SEQ ID NO: 14.

7. The lyophilised formulation of claim 1, wherein the anti-CD40 antibody comprises a heavy chain region of SEQ ID NO: 17 and a light chain region of SEQ ID NO: 18.

* * * * *

SEQUENCE LISTING

<160> NUMBER OF SEQ ID NOS: 21

<210> SEQ ID NO 1
<211> LENGTH: 120
<212> TYPE: PRT
<213> ORGANISM: Homo sapiens

<400> SEQUENCE: 1

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110
```

```
Gly Thr Leu Val Thr Val Ser Ser
        115             120

<210> SEQ ID NO 2
<211> LENGTH: 112
<212> TYPE: PRT
<213> ORGANISM: Homo sapiens

<400> SEQUENCE: 2

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
            100                 105                 110

<210> SEQ ID NO 3
<211> LENGTH: 5
<212> TYPE: PRT
<213> ORGANISM: Homo sapiens

<400> SEQUENCE: 3

Ser Tyr Gly Met His
1               5

<210> SEQ ID NO 4
<211> LENGTH: 17
<212> TYPE: PRT
<213> ORGANISM: Homo sapiens

<400> SEQUENCE: 4

Val Ile Ser Tyr Glu Glu Ser Asn Arg Tyr His Ala Asp Ser Val Lys
1               5                   10                  15

Gly

<210> SEQ ID NO 5
<211> LENGTH: 11
<212> TYPE: PRT
<213> ORGANISM: Homo sapiens

<400> SEQUENCE: 5

Asp Gly Gly Ile Ala Ala Pro Gly Pro Asp Tyr
1               5                   10

<210> SEQ ID NO 6
<211> LENGTH: 16
<212> TYPE: PRT
<213> ORGANISM: Homo sapiens

<400> SEQUENCE: 6

Arg Ser Ser Gln Ser Leu Leu Tyr Ser Asn Gly Tyr Asn Tyr Leu Asp
1               5                   10                  15
```

<210> SEQ ID NO 7
<211> LENGTH: 7
<212> TYPE: PRT
<213> ORGANISM: Homo sapiens

<400> SEQUENCE: 7

Leu Gly Ser Asn Arg Ala Ser
1               5

<210> SEQ ID NO 8
<211> LENGTH: 9
<212> TYPE: PRT
<213> ORGANISM: Homo sapiens

<400> SEQUENCE: 8

Met Gln Ala Arg Gln Thr Pro Phe Thr
1               5

<210> SEQ ID NO 9
<211> LENGTH: 450
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu

```
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Ala Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 10
<211> LENGTH: 219
<212> TYPE: PRT
<213> ORGANISM: Homo sapiens

<400> SEQUENCE: 10

Asp Ile Val Met Thr Gln Ser Pro Leu Ser Leu Thr Val Thr Pro Gly
1               5                   10                  15
Glu Pro Ala Ser Ile Ser Cys Arg Ser Ser Gln Ser Leu Leu Tyr Ser
            20                  25                  30
Asn Gly Tyr Asn Tyr Leu Asp Trp Tyr Leu Gln Lys Pro Gly Gln Ser
        35                  40                  45
Pro Gln Val Leu Ile Ser Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Arg Gln Thr Pro Phe Thr Phe Gly Pro Gly Thr Lys Val Asp Ile Arg
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
```

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 1350
<212> TYPE: DNA
<213> ORGANISM: Homo sapiens

<400> SEQUENCE: 11

```
caggtgcagc tggtggaatc tggcggcgga gtggtgcagc tggccggtc cctgagactg      60
tcttgcgccg cctccggctt caccttctcc agctacggca tgcactgggt gcgacaggcc    120
cctggcaagg gactggaatg ggtggccgtg atctcctacg aggaatccaa cagataccac    180
gctgactccg tgaagggccg gttcacaatc tcccgggaca ctccaagat caccctgtac    240
ctgcagatga actccctgcg gaccgaggac accgccgtgt actactgcgc cagggacgga    300
ggaatcgccg ctcctggacc tgattattgg ggccagggca ccctggtgac agtgtcctcc    360
gctagcacca agggcccctc cgtgttccct ctggcccct ccagcaagtc cacctctggc    420
ggcaccgccg ctctgggctg cctggtgaaa gactacttcc ccgagcccgt gaccgtgtcc    480
tggaactctg gcgccctgac ctccggcgtg cacacctttc cagccgtgct gcagtcctcc    540
ggcctgtact ccctgtcctc cgtggtgacc gtgccctcta gctctctggg cacccagacc    600
tacatctgca acgtgaacca caagccctcc aacaccaagg tggacaagcg ggtggaaccc    660
aagtcctgcg acaagaccca cacctgtccc cctgccctg ccctgaact gctgggcgga    720
ccttccgtgt tcctgttccc cccaaagccc aaggacaccc tgatgatctc ccggacccc    780
gaagtgacct gcgtggtggt ggacgtgtcc cacgaggacc ctgaagtgaa gttcaattgg    840
tacgtggacg gcgtggaagt gcacaacgcc aagaccaagc ccagagagga acagtacgcc    900
tccacctacc gggtggtgtc tgtgctgacc gtgctgcacc aggactggct gaacggcaaa    960
gagtacaagt gcaaggtctc caacaaggcc ctgcctgccc ccatcgaaaa gaccatctcc   1020
aaggccaagg gccagccccg cgagccacag gtgtacacac tgcccccag ccggaagag    1080
atgaccaaga accaggtgtc cctgacctgt ctggtcaaag cttctaccc ctccgatatc   1140
gccgtggagt gggagtccaa cggacagccc gagaacaact acaagaccac ccccctgtg    1200
ctggactccg acggctcatt cttcctgtac tccaagctga ccgtggacaa gtcccggtgg   1260
cagcagggca acgtgttctc ctgctccgtg atgcacgagg ccctgcacaa ccactacacc   1320
cagaagtccc tgtccctgag ccccggcaag                                    1350
```

<210> SEQ ID NO 12
<211> LENGTH: 657
<212> TYPE: DNA
<213> ORGANISM: Homo sapiens

<400> SEQUENCE: 12

```
gacatcgtga tgacccagtc ccccctgtcc ctgaccgtga cacctggcga gcctgcctct     60
atctcctgca gatcctccca gtccctgctg tactccaacg gctacaacta cctggactgg    120
tatctgcaga agcccggcca gtccccacag gtgctgatct ccctgggctc aacagagcc    180
tctggcgtgc ccgaccggtt ctccggctct ggctctggcc ccgacttcac actgaagatc    240
```

```
tcacgggtgg aagccgagga cgtgggcgtg tactactgca tgcaggcccg gcagaccccc    300
ttcaccttcg ccctggcac  caaggtggac atccggcgta cggtggccgc tcccagcgtg    360
ttcatcttcc ccccagcga  cgagcagctg aagagcggca ccgccagcgt ggtgtgcctg    420
ctgaacaact tctaccccc  ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc ataaggtgta cgcctgcgag    600
gtgacccacc agggcctgtc cagccccgtg accaagagct tcaacagggg cgagtgc       657
```

```
<210> SEQ ID NO 13
<211> LENGTH: 450
<212> TYPE: PRT
<213> ORGANISM: Homo sapiens

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 14
<211> LENGTH: 219
<212> TYPE: PRT
<213> ORGANISM: Homo sapiens

<400> SEQUENCE: 14

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 15
<211> LENGTH: 1350
<212> TYPE: DNA
<213> ORGANISM: Homo sapiens

<400> SEQUENCE: 15

| | | | | | |
|---|---|---|---|---|---|
| caggtgcagc | tggtggaatc | tggcggcgga | gtggtgcagc | ctggccggtc | cctgagactg | 60 |
| tcttgcgccg | cctccggctt | caccttctcc | agctacggca | tgcactgggt | gcgacaggcc | 120 |
| cctggcaagg | gactggaatg | ggtggccgtg | atctcctacg | aggaatccaa | cagataccac | 180 |
| gctgactccg | tgaagggccg | gttcacaatc | tcccgggaca | actccaagat | caccctgtac | 240 |
| ctgcagatga | actccctgcg | gaccgaggac | accgccgtgt | actactgcgc | cagggacgga | 300 |
| ggaatcgccg | ctcctggacc | tgattattgg | ggccagggca | ccctggtgac | agtgtcctcc | 360 |
| gctagcacca | agggcccctc | cgtgttccct | ctggcccct | ccagcaagtc | cacctctggc | 420 |
| ggcaccgccg | ctctgggctg | cctggtgaaa | gactacttcc | ccgagcccgt | gaccgtgtcc | 480 |
| tggaactctg | gcgccctgac | ctccggcgtg | cacacctttc | cagccgtgct | gcagtcctcc | 540 |
| ggcctgtact | ccctgtcctc | cgtggtgacc | gtgccctcta | gctctctggg | cacccagacc | 600 |
| tacatctgca | acgtgaacca | caagccctcc | aacaccaagg | tggacaagcg | ggtggaaccc | 660 |
| aagtcctgcg | acaagaccca | cacctgtccc | cctgccctg | ccctgaact | gctgggcgga | 720 |
| ccttccgtgt | tcctgttccc | cccaaagccc | aaggacaccc | tgatgatctc | ccggacccc | 780 |
| gaagtgacct | gcgtggtggt | ggccgtgtcc | cacgaggacc | ctgaagtgaa | gttcaattgg | 840 |
| tacgtggacg | gcgtggaagt | gcacaacgcc | aagaccaagc | ccagagagga | acagtacaac | 900 |
| tccacctacc | gggtggtgtc | tgtgctgacc | gtgctgcacc | aggactggct | gaacggcaaa | 960 |
| gagtacaagt | gcaaggtctc | caacaaggcc | ctgcctgccc | catcgaaaaa | gaccatctcc | 1020 |
| aaggccaagg | gccagccccg | cgagccacag | gtgtacacac | tgcccccag | ccgggaagag | 1080 |
| atgaccaaga | accaggtgtc | cctgacctgt | ctggtcaaag | gcttctaccc | ctccgatatc | 1140 |
| gccgtggagt | gggagtccaa | cggacagccc | gagaacaact | acaagaccac | ccccctgtg | 1200 |
| ctggactccg | acggctcatt | cttcctgtac | tccaagctga | ccgtggacaa | gtcccggtgg | 1260 |
| cagcagggca | acgtgttctc | ctgctccgtg | atgcacgagg | ccctgcacaa | ccactacacc | 1320 |
| cagaagtccc | tgtccctgag | ccccggcaag | | | | 1350 |

<210> SEQ ID NO 16
<211> LENGTH: 657
<212> TYPE: DNA
<213> ORGANISM: Homo sapiens

<400> SEQUENCE: 16

| | | | | | |
|---|---|---|---|---|---|
| gacatcgtga | tgacccagtc | ccccctgtcc | ctgaccgtga | cacctggcga | gcctgcctct | 60 |
| atctcctgca | gatcctccca | gtccctgctg | tactccaacg | gctacaacta | cctggactgg | 120 |
| tatctgcaga | agcccggcca | gtccccacag | gtgctgatct | ccctgggctc | caacagagcc | 180 |
| tctggcgtgc | ccgaccggtt | ctccggctct | ggctctggca | ccgacttcac | actgaagatc | 240 |
| tcacgggtgg | aagccgagga | cgtgggcgtg | tactactgca | tgcaggcccg | gcagaccccc | 300 |
| ttcaccttcg | gccctggcac | caaggtggac | atcggcgta | cggtggccgc | tcccagcgtg | 360 |
| ttcatcttcc | cccccagcga | cgagcagctg | aagagcggca | ccgccagcgt | ggtgtgcctg | 420 |
| ctgaacaact | tctaccccg | ggaggccaag | gtgcagtgga | aggtggacaa | cgccctgcag | 480 |

```
agcggcaaca gccaggagag cgtcaccgag caggacagca aggactccac ctacagcctg       540
agcagcaccc tgaccctgag caaggccgac tacgagaagc ataaggtgta cgcctgcgag       600 gtgaccacc  agggcctgtc cagccccgtg accaagagct tcaacagggg cgagtgc          657
```

<210> SEQ ID NO 17
<211> LENGTH: 450
<212> TYPE: PRT
<213> ORGANISM: Homo sapiens

<400> SEQUENCE: 17

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 18
<211> LENGTH: 219
<212> TYPE: PRT
<213> ORGANISM: Homo sapiens

<400> SEQUENCE: 18

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
                20                  25                  30

Asn Gly Tyr Asn Tyr Leu Asp Trp Tyr Leu Gln Lys Pro Gly Gln Ser
            35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 19
<211> LENGTH: 1350
<212> TYPE: DNA
<213> ORGANISM: Homo sapiens

<400> SEQUENCE: 19
caggtgcagc tggtggaatc tggcggcgga gtggtgcagc ctggccggtc cctgagactg      60

```
tcttgcgccg cctccggctt caccttctcc agctacggca tgcactgggt gcgacaggcc    120
cctggcaagg gactggaatg ggtggccgtg atctcctacg aggaatccaa cagataccac    180
gctgactccg tgaagggccg gttcacaatc tcccgggaca actccaagat caccctgtac    240
ctgcagatga actccctgcg gaccgaggac accgccgtgt actactgcgc cagggacgga    300
ggaatcgccg ctcctggacc tgattattgg ggccagggca ccctggtgac agtgtcctcc    360
gctagcacca agggcccctc cgtgttccct ctggccccct tccagcaagt ctacctccgg    420 cggcacagctg ctctgggctg cctggtcaag gactacttcc ctgagcctgt gacagtgtcc    480
tggaactctg gcgccctgac ctctggcgtg cacaccttcc ctgccgtgct gcagtcctcc    540
ggcctgtact ccctgtcctc cgtggtcaca gtgccttcaa gcagcctggg cacccagacc    600
tatatctgca acgtgaacca caagccttcc aacaccaagg tggacaagcg ggtggagcct    660
aagtcctgcg acaagaccca cacctgtcct ccctgccctg ctcctgaagc tgctggcggc    720
ccttctgtgt tcctgttccc tccaaagccc aaggacaccc tgatgatctc ccggacccct    780
gaagtgacct gcgtggtggt ggacgtgtcc cacgaggatc ctgaagtgaa gttcaattgg    840
tacgtggacg gcgtggaggt gcacaacgcc aagaccaagc ctcgggagga acagtacaac    900
tccacctacc gggtggtgtc cgtgctgacc gtgctgcacc aggactggct gaacggcaaa    960
gagtacaagt gcaaagtctc caacaaggcc ctgcctgccc ctatcgaaaa gacaatctcc   1020
aaggccaagg gccagcctag ggaaccccag gtgtacaccc tgccacccag ccgggaggaa   1080
atgaccaaga accaggtgtc cctgacctgt ctggtcaagg gcttctaccc ttccgatatc   1140
gccgtggagt gggagtctaa cggccagcct gagaacaact acaagaccac ccctcctgtg   1200
ctggactccg acggctcctt cttcctgtac tccaaactga ccgtggacaa gtcccggtgg   1260
cagcagggca acgtgttctc ctgctccgtg atgcacgagg ccctgcacaa ccactacacc   1320
cagaagtccc tgtccctgtc tcccggcaag                                    1350
```

<210> SEQ ID NO 20
<211> LENGTH: 657
<212> TYPE: DNA
<213> ORGANISM: Homo sapiens

<400> SEQUENCE: 20

```
gacatcgtga tgacccagtc ccccctgtcc ctgaccgtga cacctggcga gcctgcctct     60
atctcctgca gatcctccca gtccctgctg tactccaacg gctacaacta cctggactgg    120
tatctgcaga agcccggcca gtccccacag gtgctgatct ccctgggctc aacagagcc    180 tctggcgtgc ccgaccggtt ctccggctct ggctctggca ccgacttcac actgaagatc    240
tcacgggtgg aagccgagga cgtgggcgtg tactactgca tgcaggcccg gcagacccc    300 ttcaccttcg gccctggcac caaggtggac atcggcgta cggtggccgc tcccagcgtg    360
ttcatcttcc cccccagcga cgagcagctg aagagcggca ccgccagcgt ggtgtgcctg    420
ctgaacaact tctacccccg ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc ataaggtgta cgcctgcgag    600
gtgacccacc agggcctgtc cagccccgtg accaagagct tcaacagggg cgagtgc      657
```

<210> SEQ ID NO 21
<211> LENGTH: 277
<212> TYPE: PRT

```
<213> ORGANISM: Homo sapiens

<400> SEQUENCE: 21

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
            210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
        275
```